US006313264B1

(12) United States Patent
Caggiano et al.

(10) Patent No.: US 6,313,264 B1
(45) Date of Patent: Nov. 6, 2001

(54) EFFECTOR PROTEINS OF RAPAMYCIN

(75) Inventors: Thomas J. Caggiano, Morrisville, PA (US); Yanqiu Chen, New York, NY (US); Amedeo A. Failli, Princeton, NJ (US); Katherine L. Molnar-Kimber, Glenside, PA (US); Koji Nakanishi, New York, NY (US)

(73) Assignees: American Home Products Corporation, Madison, NJ (US); The Trustees of Columbia University, New York, NY (US)

( * ) Notice: Subject to any disclaimer, the term of this patent is extended or adjusted under 35 U.S.C. 154(b) by 0 days.

(21) Appl. No.: 08/471,112

(22) Filed: Jun. 6, 1995

Related U.S. Application Data

(63) Continuation-in-part of application No. 08/384,524, filed on Feb. 13, 1995, now abandoned, which is a continuation-in-part of application No. 08/312,023, filed on Sep. 26, 1994, now abandoned, which is a continuation-in-part of application No. 08/207,975, filed on Mar. 8, 1994, now abandoned.

(51) Int. Cl.$^7$ .................................................. C07K 17/00
(52) U.S. Cl. ......................................... 530/350; 435/183
(58) Field of Search ........................ 530/350; 435/69.1, 435/7.1, 7.6, 7.8

(56) References Cited

U.S. PATENT DOCUMENTS 5,109,112  4/1992  Siekierka et al. .

FOREIGN PATENT DOCUMENTS

| 0379342 | 7/1990 | (EP) . |
| 9218527 | 10/1992 | (WO) . |
| 9219745 | 11/1992 | (WO) . |
| 9307269 | 4/1993 | (WO) . |
| 9325533 | 12/1993 | (WO) . |

OTHER PUBLICATIONS

Brown, E.J., et al. (1994) *Nature* 369: 756–58.*
Kunz, J., et al. (1993) *Cell* 73: 585–96.*
Sabatini, P. M., et al. (1994) *Cell* 78: 35–43.*
Sabers, C. J., et al. (1995) *J. Biol. Chem.* 270: 815–22.*
Chiu, M. I., et al. (1994) *Proc. Natl. Acad. Sci. USA.* 91: 12574–78.*
Sehgal et al., "Rapamune (Sirolimus, Rapamycin): An Overview and Mechanism of Action," *Therapeutic Drug Monitoring* 17:660–665 (1995).
Jon Clardy, "The chemistry of signal transduction," *Proc. Natl. Acad. Sci. USA* 92:56–61 (1995).

Chen et al., "Identification of an 11–kDa FKBP12–rapamycin–binding domain within the 289–kDa FKBP12–rapamycin–associated protein and characterization of a critical serine residue," *Proc. Natl. Acad. Sci. USA* 92:4947–4951 (1995).
Erdjument–Bromage et al., "High–sensitivity sequencing of large proteins: Partial structure of the rapamycin–FKBP12 target," *Protein Science* 3:2435–2446 (1994).
Belshaw et al., "Synthesis, Structure and Mechanism in Immunophilin Research," *Synlett* (6):381–464 (1994).
Kunz and Hall, "Cyclosporin A, FK506 and rapamycin: more than just immunosuppression," *Trends in Biochemical Sciences* 18:334–338 (1993).
Partaledis et al., "*Saccharomyces cerevisiae* Contains a Homolog of Human FKBP–13, a Membrane–associated FK506/Rapamycin Binding Protein," *Yeast* 8:673–680 (1992).
Sehgal et al., Medicinal Research Reviews, vol. 14, No. 1, 1–22 (1994).
Heitman et al., Reports, 253, 905–909 (1991).
Ocain et al., Biochem. and Biophys. Res. Comm., 192 (3), 1340–1346, (1993).
Liu et al., Cell, vol. 66, 807–815 (1991).
Armistead et al., Annual Rpt. in Med. Chem., 28, 207–215 (1993).
Rosen et al., Angew. Chem. Int. Ed. Engl., 31, 384–400 (1992).
Cafferkey et al., Molecular and Cellular Biology, 13 (10), 6012–6023, 1993.
Liu, TiPS, vol. 14, 182–188 (May 1993).
Kunz et al., Cell, vol. 73, 585–596 (1993).
Murthy et al., Clin. Chem. vol. 38, No. 7, 1307–1310 (1992).
Current Opinion in Therapeutic Patents, pp. 37–38, Jan. 1992.
Kivisto, Clin. Pharmacokinet., 23 (3), 173–190 (1992).
Milligan et al., J. Med. Chem., 36 (14), 1923–1937 (1993).

* cited by examiner

*Primary Examiner*—Ponnathapu Achutamurty
*Assistant Examiner*—Kathleen Kerr
(74) *Attorney, Agent, or Firm*—Finnegan, Henderson, Farabow, Garrett & Dunner, L.L.P.

(57) ABSTRACT

This invention comprises novel Rapamycin-FKBP12 binding proteins of mammalian origin for identification, design and synthesis of immunomodulatory, anti-restenosis or anti-tumor agents, as well as fragments of the proteins and the DNA, cDNA, antisense RNA and DNA segments corresponding to the proteins. This invention also comprises methods for isolating the proteins and therapeutic uses related to the proteins.

2 Claims, No Drawings

EFFECTOR PROTEINS OF RAPAMYCIN

RELATED APPLICATIONS

This application is a continuation-in-part of patent application Ser. No. 08/384,524, filed Feb. 13, 1995, now abandoned, which is a continuation-in-part of patent application Ser. No. 08/312,023, filed Sep. 26, 1994, now abandoned, which is a continuation-in-part of patent application Ser. No. 08/207,975, filed Mar. 8, 1994, now abandoned.

This invention concerns effect or proteins of Rapamycin. More particularly, this invention concerns novel Rapamycin-FKBP12 binding proteins of mammalian origin for identification, design and synthesis of immunomodulatory, anti-restenosis or anti-tumor agents.

BACKGROUND OF THE INVENTION

Rapamycin is a macrolide antibiotic produced by *Streptomyces hygroscopicus* which was first characterized via its properties as an antifungal agent. It adversely affects the growth of fungi such as *Candida albicans* and *Microsporum gypseum*. Rapamycin, its preparation and its antibiotic activity were described in U.S. Pat. No. 3,929,992, issued Dec. 30, 1975 to Surendra Sehgal et al. In 1977 Martel, R. R. et al. reported on immunosuppressive properties of rapamycin against experimental allergic encephalitis and adjuvant arthritis in the Canadian Journal of Physiological Pharmacology, 55, 48–51 (1977). In 1989, Calne, R. Y. et al. in Lancet, 1989, no. 2, p. 227 and Morris, R. E. and Meiser, B. M. in Medicinal Science Research, 1989, No. 17, P. 609–10, separately reported on the effectiveness of raparnycin in inhibiting rejection in vivo in allograft transplantation. Numerous articles have followed describing the immunosuppressive and rejection inhibiting properties of rapamycin, and clinical investigation has begun for the use of rapamycin in inhibiting rejection in transplantation in man.

Rapamycin alone (U.S. Pat. No. 4,885,171) or in combination with picibanil (U.S. Pat. No. 4,401,653) has been shown to have antitumor activity. R. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], and smooth muscle cell proliferation and intimal thickening following vascular injury [Morris, R. J. Heart Lung Transplant 11 (pt. 2): 197 (1992)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions. U.S. Pat. No. 5,118,678 discloses carbamates of rapamycin that are useful as immunosuppressive, anti-inflammatory, antifungal, and antitumor agents. U.S. Pat. No. 5,100,883 discloses fluorinated esters of rapamycin. U.S. Pat. No. 5,118,677 discloses amide esters of rapamycin. U.S. Pat. No. 5,130,307 discloses aminoesters of rapamycin. U.S. Pat. No. 5,117,203 discloses sulfonates and sulfamates of rapamycin. U.S. Pat. No. 5,194,447 discloses sulfonylcarbamates of rapamycin.

U.S. Pat. No. 5,100,899 (Calne) discloses methods of inhibiting transplant rejection in mammals using rapamycin and derivatives and prodrugs thereof. Other chemotherapeutic agents listed for use with rapamycin are azathioprine, corticosteroids, cyclosporin (and cyclosporin A), and FK-506, or any combination thereof.

Rapamycin produces immunosuppressive effects by blocking intracellular signal transduction. Rapamycin appears to interfere with a calcium independent signalling cascade in T cells and mast cells [Schreiber et al. (1992) Tetrahedron 48:2545–2558]. Rapamycin has been shown to bind to certain immunophilins which are members of the FK-506 binding proteins (FKBP) family. In particular, Rapamycin has been shown to bind to the binding proteins, FKBP12, FKBP13, FKBP25 [Galat A. et al., (1992) Biochemistry 31(8);2427–2437 and Ferrera A, et al., (1992) Gene 113(1):125–127; Armistead and Harding, Ann. Reports in Med. Chem. 28:207–215, 1993], and FKBP52 [WO 93/07269].

Rapamycin is able to inhibit mitogen-induced T cell and B cell proliferation as well as proliferation induced by several cytokines, including IL-2, IL-3, IL-4 and IL-6 (reviewed by Sehgal et al., Med. Research Rev.14: 1–22, 1994). It can also inhibit antibody production. Rapamycin has been shown to block the cytokine-induced activation of $p70^{S6}$ kinase which appears to correlate with Rapamycin's ability to decrease protein synthesis accompanying cell cycle progression (Calvo et al., Proc. Natl. Acad. Sci. USA, 89:7571–7575,1992; Chung et al., Cell 69:1227–1236, 1992; Kuo et al., Nature 358:70–73,1992; Price et al., Science 257:973–977, 1992). It also inhibits the activation of cdk2/cyclin E complex (Flanagan et al., Ann. N.Y.Acad. Sci, in press; Flanagan et al, Mol. Cell biol., in press; Flanagan et al., J.Cell Biochem. 17A:292, 1993). Rapamycin's effects are not mediated by direct binding to $p70^{s6}$ kinase and cdk2/cyclin E, but by action of the Rapamycin-FKBP complex on upstream component(s) which regulate the activation status of the kinases.

It is generally accepted that the action of immunosuppressive drugs, such as Rapamycin, cyclosporine and FK506, is dependent upon the formation of a complex with their respective intracellular receptor proteins called immunophilins. While the binding of these immunosuppressants with their respective immunophilins inhibits the cis-trans peptidyl prolyl isomerase (PPIase) activity of immunophilins, PPIase inhibition is not sufficient to mediate the immunosuppressive activity (reviewed in Armistead and Harding, Annual Reports in Med. Chem, 28:207–215:1993). Two rapamycin analogs which are Diels Alder adducts, one with 4-phenyl-1,2,4-triazoline-3,5-dione, and the second with 4-methyl-1,2,4-triazoline-3,5-dione, bind to FKBP, inhibited its PPIase activity, yet they did not exhibit any detectable immunosuppressive activity. The phenyl-triazolinedione Diels Alder adduct at high molar excess has been shown to competitively inhibit rapamycin's effect on DNA synthesis in mitogen-stimulated murine thymocyte proliferation (Ocain et al., Biochem. Biophys. Res. Commun. 192:1340, 1993). Recent evidence suggests that the binary immunophilin-drug complex such as cyclophilin-cyclosporin A and FKBP-FK506 gains a new function that enables it to block signal transduction by acting on specific target proteins. The molecular target of both cyclophilin-cyclosporin A and FKBP-FK506 complexes such as has been identified as the $Ca^{+2}$/calmodulin dependent serine/threonine phosphatase calcineurin (J. Liu et al, Cell 66, 807, 1991; J. Liu et al, Biochemistry 31, 3896, 1992; W. M. Flanagan, et al., Nature 352, 803, 1992; McCaffrey et al., J. Biol. Chem. 268, 3747, 1993; McCaffrey et al., Science 262:750, 1993).

Rapamycin's antifungal and immunosuppressive activities are mediated via a complex consisting of Rapamycin, a member of the FK506 binding protein (FKBP) family and at least one additional third protein, called the target of Rapamycin (TOR). The family of FKBPs is reviewed by Armistead and Harding (Annual Reports in Med. Chem, 28:207–215:1993). The relevant FKBP molecule in Rapamycin's antifungal activity has been shown to be FKBP12 (Heitman et al., Science 253:905–909:1993). In mammalian cells, the relevant FKBPs are being investigated. Although two TOR proteins (TOR1 and TOR2) have been identified in yeast (Kunz et al., Cell 73:585–596:1993), the target of Rapamycin in human cells remains elusive. The carboxy terminus of yeast TOR2 has been shown to exhibit 20% identity with two proteins, the p110 subunit of phosphatidylinositol 3-kinase and VPS34, a yeast vacuolar sorting protein also shown to have PI 3K activity. However, J. Blenis et al. (AAI meeting, May, 1993) have reported that Rapamycin-FKBP12 complex does not directly mediate its effects on PDGF stimulated cells via the p110, p85 PI 3K complex.

DESCRIPTION OF THE INVENTION

This invention concerns isolated, cloned and expressed proteins which bind to a complex of GST-FKBP12-Rapamycin. These proteins are isolated from membrane preparations of Molt 4 T cell leukemia. The sizes of the four novel proteins are estimated by PAGE migration to be 125±12 kilodaltons (kDa), 148±14 kDa, 208±15 kDa and 210±20 kDa and will be referred to herein and in the claims that follow, as the 125 kDa, 148 kDa, 208 kDa, and 210 kDa, respectively. The four proteins may also be referred to herein as effect or proteins.

The proteins of this invention can be used in screening assays, such as enzyme inhibitor assays and binding assays, to identify endogenous complexes and ligands and novel exogenous compounds (like Rapamycin) which modulate their functions. They can also be used in assays to identify compounds with therapeutic benefit for restenosis, immunomodulation and as antitumor agents. Cloning the proteins of this invention does not only allow the production of large quantities of the proteins, it also provides a basis for the development of related anti-sense therapeutics. The use of cDNA clones to generate anti-sense therapeutics with immunomodulatory activity (for use against transplantation rejection, graft versus host disease, autoimmune diseases such as lupus, myasthenia gravis, multiple sclerosis, rheumatoid arthritis, type I diabetes, and diseases of inflammation such as psoriasis, dermitis, eczema, seborrhea, inflammatory bowel disease, pulmonary inflammation, asthma, and eye uveitis), antirestenosis and anti-tumor activity is included within the scope of this invention.

The proteins of the present invention can be isolated from mammalian cells, such as cells of the T cell leukemia cell line, Molt 4 (ATCC 1582, American Type Cell Culture, 12301 Parklawn Drive, Rockville, Md., USA, 20852), the B cell lymphoma, BJAB, or normal human T cells. These mammalian cells can be lysed in a buffer containing protease inhibitors and reducing agent (2-ME), such as hypotonic buffer A (100 mM HEPES, pH 7.5, 20 mM KCl, 1 mM EDTA, 0.4 mM PMSF and 2 mM beta mercaptoethanol (2-ME)). The cell nuclei and unbroken cells are cleared by centrifugation at a temperature which minimizes protein degradation. The membrane fraction of the cells can then be concentrated or pelleted by ultracentrifugation at 100,000 g. Detergent solubilization of the membrane pellet is carried out in a detergent containing buffer such as buffer B (50 mM Tris, pH 7.2, 100 mM NaCl, 20 mM KCl, 0.2 mM PMSF, 1 mM 2-ME, 2 mM $CaCl_2$, 2 mM $MgCl_2$, 5 µg/ml aprotinin, leupeptin, pepstatin A and antipain), containing CHAPSO (3-[(3-cholamidopropyl)dimethylammonio]-1-propane sulfonate; 12 mM) or Triton X100 (polyethylene glycol 4-isooctylphenyl ether). The solubilized membrane proteins can then be separated from the debris by 100,000 g ultracentrifugation at a temperature which minimizes protein degradation. The supernatant containing solubilized membrane proteins is then preabsorbed with an affinity resin, such as glutathione resin, in the presence of protease inhibitors at a temperature which minimizes protein degradation. After centrifugation to remove the resin from the supernatant, the supernatant is then incubated with complexed Rapamycin or Rapamycin analog to FKBP, such as GST-FKBP12—Rapamycin at a temperature which minimizes protein degradation. The mixture of solubilized membrane proteins, incubated with complexed Rapamycin or Rapamycin analog to FKBP, such as GST-FKBP12—Rapamycin, can then be incubated with the affinity resin to bind the complexes of rapamycin or rapamycin analog, FKBP fusion protein and binding proteins at a temperature which minimizes protein degradation. After most non-specific proteins are rinsed away using a detergent containing buffer, such as Buffer C (50 mM Tris, pH 7.2, 100 mM NaCl, 20 mM KCl, 0.2 mM PMSF, 1 mM 2-ME or 10 mM dithiothreitol, 0–5 mM $CaCl_2$, 0–5 mM $MgCl_2$, 5 µg/ml aprotinin, leupeptin, pepstatin A and antipain and 0.1% Triton X100) (Polyethylene glycol 4-isooctyl phenyl ether), the proteins are eluted from the resin under denaturing conditions, such as a buffer containing sufficient detergent to dissociate it from resin (e.g. Laemli buffer with or without glycerol or dye, as described by Laemli, Nature 227:680, 1970), or non-denaturing conditions such as a buffer containing an appropriate eluting compound for the affinity column, such as 5 mM glutathione. The proteins can then be separated by size using SDS polyacrylamide gel electrophoresis (SDS-PAGE).

The present invention also includes the genomic DNA sequences for the abovementioned proteins, as well as the cDNA and anti-sense RNA and DNA sequences which correspond to the genes for the abovementioned proteins. The present invention further includes the proteins of other mammalian species which are homologous or equivalent at least in function to the abovementioned proteins, as well as the DNA gene sequences for the homologous or equivalent proteins and the cDNA and anti-sense RNA and DNA sequences which correspond to the genes for the homologous or equivalent proteins.

For the purposes of this disclosure and the claims that follow, equivalents of the proteins of this invention are considered to be proteins, protein fragments and/or truncated forms with substantially similar, but not identical, amino acid sequences to the proteins mentioned above, the equivalents exhibiting rapamycin-FKBP complex binding characteristics and function similar to the proteins mentioned above. Therefore, in this specification and the claims below, references to the 125 kDa, 148 kDa, 208 kDa, and 210 kDa proteins of this invention are also to be understood to indicate and encompass homologous or equivalent proteins, as well as fragmented and/or truncated forms with substantially similar, but not identical, amino acid sequences of the 125 kDa, 148 kDa, 208 kDa, and 210 kDa proteins mentioned above.

These proteins or protein homologues or equivalents can be generated by similar isolation procedures from different cell types and/or by recombinant DNA methods and may be modified by techniques including site directed mutagenesis. For example, the genes of this invention can be engineered to express one or all of the proteins as a fusion protein with the fusion partner giving an advantage in isolation (e.g. HIS oligomer, immunoglobulin Fc, glutathione S-transferase, FLAG etc). Mutations or truncations which result in a soluble form can also be generated by site directed mutagenesis and would give advantages in isolation.

This invention further includes oligopeptide fragments, truncated forms and protein fragments that retain binding affinity yet have less than the active protein's amino acid sequences. This invention also includes monoclonal and polyclonal antibodies specific for the proteins and their uses. Such uses include methods for screening for novel agents for immunomodulation and/or anti-tumor activity and methods of measuring the parent compound and/or metabolites in biological samples obtained from individuals taking immunosuppressive drugs. The use of the cDNA clone to generate anti-sense therapeutics (Milligan et al, J. Med. Chem. 36:1923–1936, 1993) with immunomodulatory activity (transplantation rejection, graft versus host disease, autoimmune diseases such as lupus, myasthenia gravis, multiple sclerosis, rheumatoid arthritis, type I diabetes, and diseases of inflammmation such as psoriasis, dermitis, eczema, seborrhea, inflammatory bowel disease, pulmonary inflammation, asthma, and eye uveitis), and anti-tumor activity is also included in the present invention.

The proteins of this invention can also be made by recombinant DNA techniques familiar to those skilled in the art. That is, the gene of the protein in question can be cloned by obtaining a partial amino acid sequence by digestion of the protein with a protease, such as Lysine C, and isolating the resulting protein fragments by microbore HPLC, followed by fragment sequencing (Matsudaira in A Practical Guide to Protein and Peptide Purification for Microsequencing, Academic Press (San Diego, Calif., 1989)). The determined sequence can then be used to make oligonucleotide probes which can be used to screen a human cDNA library directly or generate probes by polymerase chain reaction. The library can be generated from human T cells or the cell lines, Molt 4, Jurkat, or other etc. to obtain clones. These clones can be used to identify additional clones containing additional sequences until the protein's full gene, i.e. complete open reading frame, is cloned.

It is known in the art that some proteins can be encoded by an open reading frame which is longer than initially predicted by the size of the protein. These proteins may represent cleavage products of the precursor protein translated from the complete open reading frame (eg. IL-1 beta) or proteins translated using a downstream start codon (eg. Hepaptitis B surface antigen). In view of this knowledge, it is understood that the term cDNA as used herein and in the claims below refers to cDNA for the gene's complete open reading frame or any portions thereof which may code for a protein of this invention or the protein's fragments, together or separate, or truncated forms, as previously discussed.

In a complementary strategy, the gene(s) for the proteins of this invention may be identified by interactive yeast cloning techniques using FKBP12:RAPA as a trap for cloning. These strategies can also be combined to quicken the identification of the clones.

The relevant cDNA clone encoding the gene for any of the four proteins can also be expressed in E. coli, yeast, or baculovirus infected cells or mammalian cells using state of the art expression vectors. Isolation can be performed as above or the cDNA can be made as a fusion protein with the fusion partner giving an advantage in isolation (e.g. HIS oligomer, immunoglobulin Fc, glutathione S-transferase, etc). Mutations which result in a soluble form can also be generated by site directed mutagenesis and would give advantages in isolation.

The uses of such cDNA clones include production of recombinant proteins. Further, such recombinant proteins, or the corresponding natural proteins isolated from mammalian cells, or fragments thereof (including peptide oligomers) are useful in generation of antibodies to these proteins. Briefly, monoclonal or polyclonal antibodies are induced by immunization with recombinant proteins, or the corresponding natural proteins isolated from mammalian cells, or fragments thereof (including peptide oligomers conjugated to a carrier protein (e.g. keyhole limpet hemocyanin or bovine serum albumin)) of animals using state of the art techniques. The antibodies can be used in the purification process of the natural proteins isolated from mammalian cells or recombinant proteins from E. coli, yeast, or baculovirus infected cells or mammalian cells, or cell products.

The uses of such cDNA clones include production of recombinant proteins. Further, such recombinant proteins, or the corresponding natural proteins isolated from mammalian cells, are useful in methods of screening for novel agents such as synthetic compounds, natural products, exogenous or endogenous substrates for immunomodulation and/or antitumor activity. The natural products which may be screened may include, but are not limited to, cell lysates, cell supernatants, plant extracts and the natural broths of fungi or bacteria. As an example of a competitive binding assay, one of these proteins attached to a matrix (either covalently or noncovalently) can be incubated with a buffer containing the compounds, natural products, cell lysates or cell supernatants and a labeled rapamycin:FKBP complex. The ability of the compound, natural products, exogenous or endogenous substrates to competitively inhibit the binding of the complex or specific antibody can be assessed. Examples of methods for labeling the complex include radiolabeling, fluorescent or chemiluminescent tags, fusion proteins with FKBP such as luciferase, and conjugation to enzymes such as horse radish peroxidase, alkaline phosphatase, acetylcholine esterase (ACHE), etc. As an example of an enzymatic assay, the proteins are incubated in the presence or absence of novel agents such as synthetic compounds, natural products, exogenous or endogenous substrates with substrate and the enzymatic activity of the protein can be assessed. Methods of measuring the parent compound and/or metabolites in biological samples obtained from individuals taking immunosuppressive drugs can also be assessed using these proteins.

This invention includes a method for identifying substances which may be useful as immunomodulatory agents or anti-tumor agents, the method utilizing the following steps:

a) combining the substance to be tested with one of the four mammalian proteins (125 kDa, 148 kDa, 208 kDa or 210 kDa) of this invention, with the protein being bound to a solid support:

b) maintaining the substance to be tested and the protein bound to the solid support of step (a) under conditions appropriate for binding of the substance to be tested with the protein, and c) determining whether binding of the substance to be tested occurred in step (b).

This invention also includes a method for identifying substances which may be useful as immunomodulatory or anti-tumor agents which involves the following steps:

a) combining a substance to be tested with one of the mammalian proteins of this invention, the protein being bound to a solid support:

b) maintaining the substance to be tested and the protein bound to the solid support of step (a) under conditions appropriate for binding of the substance to be tested with the protein, and c) determining whether the presence of the substance to be tested modulated the activity of the mammalian protein.

This invention further includes a method for detecting, in a biological sample, rapamycin, rapamycin analogs or rapamycin metabolites which, when complexed with a FKBP, bind to one of the four listed proteins of this invention, the method comprising the steps of:

a) combining the biological sample with a FKBP to form a first mixture containing, if rapamycin, rapamycin analogs or rapamycin metabolites are present in the biological sample, a rapamycin:FKBP complexes, rapamycin analog:FKBP complexes, or rapamycin metabolite:FKBP complexes;

b) creating a second mixture by adding the first mixture to one of the proteins of this invention, the protein bound to a solid support;

c) maintaining the second mixture of step (b) under conditions appropriate for binding the rapamycin-:FKBP complexes, rapamycin analog:FKBP complexes, or rapamycin metabolite:FKBP complexes, if present, to the protein of this invention; and d) determining whether binding of the rapamycin:FKBP complexes, rapamycin analog:FKBP complexes, or rapamycin metabolite:FKBP complexes and the protein occurred in step (c).

Also included in this invention is the use of the cDNA clones to generate anti-sense therapeutics. This can be accomplished by using state of the art techniques, such as those described in Milligan et al, J. Med. Chem. 36:14:1924–1936. For the purposes of this disclosure and the claims that follow, antisense RNA and DNA are understood to include those RNA and DNA strands derived from a cDNA clone which encodes for one of the four proteins (125 kDa, 148 kDa, 208 kDa or 210 kDa) of the present invention which have a native backbone or those which utilize a modified backbone. Such modifications of the RNA and DNA backbones are described in Milligan et al, J. Med. Chem. 36:14:1924–1936. The antisense compounds created by the state of the art techniques recently described (Milligan et al, J. Med. Chem. 36:14:1924–1936) can be useful in modulating the immune response and thus useful in the treatment or inhibition of transplantation rejection such as kidney, heart, liver, lung, bone marrow, pancreas (islet cells), cornea, small bowel, and skin allografts, and heart valve xenografts; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, and eye uveitis. The antisense molecules of this invention can have antitumor, antifungal activities, and antiproliferative activities. The compounds of this invention therefore can be also useful in treating solid tumors, adult T-cell leukemia/lymphoma, fungal infections, and hyperproliferative vascular diseases such as restenosis and atherosclerosis. Thus, the present invention also comprises methods for treating the abovementioned maladies and conditions in mammals, preferably in humans. The method comprises administering to a mammal in need thereof an effective amount of the relevant antisense therapeutic agent of this invention.

When administered for the treatment or inhibition of the above disease states, the antisense molecules of this invention can be administered to a mammal orally, parenterally, intranasally, intrabronchially, transdermally, topically, intravaginally, or rectally.

It is contemplated that when the antisense molecules of this invention are used as an immunosuppressive or antiinflammatory agent, they can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, and ATG. By combining the complexes of this invention with such other drugs or agents for inducing immunosuppression or treating inflammatory conditions, the lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23: 507 (1991)].

Treatment with these antisense compounds will generally be initiated with small dosages less than the optimum dose of the compound. Thereafter the dosage is increased until the optimum effect under the circumstances is reached. Precise dosages will be determined by the administering physician based on experience with the individual subject treated. In general, the antisense compounds of this invention are most desirably administered at a concentration that will afford effective results without causing any harmful or deleterious side effects.

In light of the therapeutic value of the abovementioned antisense compounds, this invention also includes pharmaceutical compositions containing the antisense RNA and antisense DNA compounds derived from cDNA clones which encode for the 125 kDa, 148 kDa, 208 kDa and 210 kDa proteins of this invention.

This invention also comprises the following process for isolating the proteins of this invention, as well as the proteins isolated therefrom:

A process for isolating proteins from mammalian cells, the process comprising the steps of:

1. The mammalian cells of interest are grown and harvested. As mentioned previously, the cells may be of T cell origin (e.g. T cell lymphomas, leukemias, normal human T cells), B cell origin (e.g. EBV transformed B cells, normal human B cells), mast cells, or other cell sources sensitive to rapamycin. The cells may be processed shortly after harvesting or may be stored frozen, such as in pellets, prior to processing. The cells which are kept frozen may be stored in a dry ice and ethanol bath, stored frozen at −70–80° C. until use. This step of growing and harvesting the cells of interest may be seen as the first step of this process or as merely preparatory for the present process.

2. Cells are lysed in a buffer containing a buffering agent (e.g. HEPES, Tris, pH 7.5), low salt (e.g.10–50 mM NaCl or KCl), chelating agent (e.g. 1–2 mM EDTA), protease inhibitors (e.g.0.4 mM PMSF) and a reducing agent (e.g. 2 mM 2-ME or 1–20 mM Dithiothreitol) at a temperature which minimizes protein degradation (e.g. 4 ° C.). It should be understood that the mammalian cells may be treated in any manner capable of producing cell lysis, including sonic lysis and douncing.

3. Unbroken cells and cell nuclei are precleared from lysates by centrifugation at a temperature which minimizes protein degradation (e.g. 4 ° C.). Centrifugation at, for example, 1600 g for 10 minutes has been found sufficient to preclear the unbroken cells and cell nuclei from the lysates. This step, while not mandatory, provides a clearer preparation for the steps that follow.

4. The membrane fraction in the precleared lysate is then concentrated, such as by ultracentrifugation. An example of this concentration would be ultracentrifugation at 100,000 g for 1–1.5 hours.

5. The membrane proteins (e.g. transmembrane, integral and membrane associated proteins) are then solubilized. This may be accomplished by incubating the pellet of Step 4 in a buffer containing a detergent which solubilizes the proteins without detrimentally denaturing them, a buffering agent (e.g. 20–50 mM Tris or HEPES, pH 7.2), salt (e.g. 100–200 mM NaCl+20 mM KCl), reducing agent (e.g. 1–2 mM 2-ME or 1–20 mM dithiothreitol), protease inhibitors (e.g. 0.2 mM PMSF, 5 μg/ml aprotinin, leupeptin, pepstatin A and antipain), divalent cations (e.g. 0–5 mM $CaCl_2$, 0–5 mM $MgCl_2$) at a temperature which minimizes protein degradation (e.g. 4° C.) . Examples of detergents useful in this step are CHAPSO (3-[(3-cholamidopropyl) dimethylammonio]-1-propane sulfonate) or Triton X100 (polyethylene glycol 4-isooctylphenyl ether). After this step, the mixture contains solubilized membrane proteins and non-solubilized cellular debris.

6. The solubilized membrane proteins are separated from the non-solubilized cellular debris, such as by ultracentrifugation (eg 100,000 g for 1–1.5 hours) at a temperature which minimizes protein degradation (e.g. 4° C.).

7. The supernatant containing solubilized membrane proteins is incubated with an affinity resin in a buffer containing a buffering agent (e.g.20–50 mM Tris or HEPES, pH 7.2), salt (e.g. 100–200 mM NaCl+20 mM KCl), reducing agent (e.g. 1–2 mM 2-ME or 10–20 mM dithiothreitol), protease inhibitors (e.g. 0.2 mM PMSF, 5 μg/ml aprotinin, leupeptin, pepstatin A and antipain), divalent cations (e.g. 0–5 mM $CaCl_2$, 0–5 mM $MgCl_2$) at a temperature and time which allows the absorption of the proteins which bind to affinity resin directly, and minimizes protein degradation (e.g. 4° C.).

8. The resin is then removed from the supernatant by centrifugation at a temperature which minimizes protein degradation (e.g. 4° C.).

9. The supernatant is then incubated with Rapamycin or Rapamycin analog (IC50 in LAF<500 nM) complexed to fusion protein of FKBP12+protein which enhances the isolation of the desired effect or protein and through which the fusion protein binds to an affinity resin or affinity column, such as GST-FKBP12, Histidine oligomer-FKBP12, biotin-FKBP12, etc., in a buffer containing a buffering agent (e.g. 20–50 mM Tris or HEPES, pH 7.2), salt (e.g. 100–200 mM NaCl+20 mM KCl), reducing agent (e.g. 1–2 mM 2-ME or 1–20 mM dithiothreitol), protease inhibitors (e.g. 0.2 mM PMSF, 5 μg/ml aprotinin, leupeptin, pepstatin A and antipain), divalent cations (e.g. 0–5 mM $CaCl_2$, 0–5 mM $MgCl_2$) at a temperature and for a time which allows binding of the effect or proteins to the fusion FKBP protein:Rapamycin or analog complexes and minimizes protein degradation (e.g. 4° C. and 1–2 hours).

10. The mixture of Step 9 containing the effect or proteins and fusion FKBP protein:Rapamycin complexes is incubated with an affinity resin at a temperature and for a time which allows binding of the complexes of the effect or proteins and fusion FKBP protein:Rapamycin or analog to the affinity resin and minimizes protein degradation (e.g. 4° C. and 0.5–2 hours).

11. Most non-specific proteins are rinsed away from the resin using a buffer which dissociates binding of non-specific proteins but not the complex between the desired proteins and RAPA-FKBP, such as a buffer containing a buffering agent (e.g.20–50 mM Tris or HEPES, pH 7.2), salts (e.g. 100–1000 mM NaCl, KCl), reducing agent (e.g. 1–2 mM 2-ME or 10–20 mM dithiothreitol), protease inhibitors (e.g. 0.2 mM PMSF, 5 μg/ml aprotinin, leupeptin, pepstatin A and antipain), divalent cations (e.g. 0–5 mM $CaCl_2$, 0–5 mM $MgCl_2$) and detergent which dissociates binding of non-specific proteins but not the complex between the four proteins and RAPA-fusion FKBP protein such as Triton X100 (Polyethylene glycol 4-isooctyl phenyl ether).

12. The effect or proteins and the fusion FKBP protein:Rapamycin complexes are eluted from the resin using an appropriate buffer, such as a buffer containing sufficient detergent to dissociate it from resin (e.g. Laemli buffer with or without glycerol or dye, Laemli, Nature 227:680, 1970), or an appropriate eluting compound for the affinity column, such as glutathione, histidine.

13. The effect or proteins can then be separated by size. This may be accomplished in any manner which separates the proteins by size, including, but not limited to, polyacrylamide gel electrophoresis and size exclusion column chromatography.

It might also be useful to compare the proteins isolated by a control procedure, that is a procedure which substitutes buffer for the rapamycin or rapamycin analog with an $IC_{50}$ in LAF<500 nM in step 8, can be used to more easily distinguish proteins which bind to the rapamycin:FKBP complex.

The proteins of this invention can also be made by recombinant DNA techniques familiar to those skilled in the art. That is, the gene of the protein in question can be cloned by obtaining a partial amino acid sequence by digestion of the protein with an appropriate endopeptidase, such as Lysine C, and isolating the resulting protein fragments by microbore HPLC, followed by fragment sequencing (Matsudaira in A Practical Guide to Protein and Peptide Purification for Microsequencing, Academic Press, San Diego, Calif. 1989). The determined sequence can then be used to make oligonucleotide probes which can be used to screen a human cDNA library, such as those for human T cells, Molt 4, Jurkat, etc, to obtain clones. (Sambrook, Fritsch, and Maniatas, Molecular Cloning, A Laboratory Manual, Cold Spring Harbor Press, 1989). These clones can be used to identify additional clones containing additional sequences until the proteins full gene is cloned (Sambrook, Fritsch, and Maniatas, Molecular Cloning, A Laboratory Manual, Cold Spring Harbor Press, 1989). In a complementary strategy, the gene(s) may be identified by interactive yeast cloning techniques using FKBP12:RAPA as a trap for cloning (Chien et al., Proc. Natl. Acad. Sci. 88: 9578–9582, 1991). These strategies can also be combined to quicken the identification of the clones.

The relevant cDNA clone can also be expressed in *E. coli*, yeast, or baculovirus infected cells or mammalian cells using state of the art expression vectors. Isolation can be performed as above or the cDNA can be made as a fusion protein with the fusion partner giving an advantage in isolation (e.g. HIS oligomer, immunoglobulin Fc, glutathione S-transferase, etc). Mutations which result in a soluble form can also be generated by site directed mutagenesis and would give advantages in isolation.

Homologs in the mouse, rat, monkey, dog and other mammalian species can be obtained using similar procedures. In addition, upon isolation of the human clone of the proteins, the clone can be used to screen for homologs in other mammalian species. These homologs can also be used to develop binding assays and to set up high through put screening assays for compounds, endogenous ligands, exogenous ligands with immunomodulatory activity.

Compounds, endogenous ligands and exogenous ligands having such immunomodulatory activity would can be useful in modulating the immune response and thus useful in the treatment or inhibition of transplantation rejection such as kidney, heart, liver, lung, bone marrow, pancreas (islet cells), cornea, small bowel, and skin allografts, and heart valve xenografts; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, and eye uveitis.

The compounds, endogenous ligands and exogenous ligands mentioned above can also have antitumor, antifungal activities, and antiproliferative activities. The compounds of this invention therefore can be also useful in treating solid tumors, adult T-cell leukemia/lymphoma, fungal infections, and hyperproliferative vascular diseases such as restenosis and atherosclerosis.

EXAMPLE 1

The proteins of the present invention were isolated utilizing a fusion protein of glutathione S-transferase—FK506 binding protein12 (GST-FKBP). GST-FKBP is produced by a recombinant *E. coli* containing the plasmid, pGEX-PKBP. The cells were grown, induced with IPTG and the fusion protein was isolated using standard technology described in D. B. Smith and K. S. Johnson, Gene 67, 31, 1988 and K. L. Guan and J. E. Dixon, Anal. Biochem. 192, 262, 1991. The solution containing glutathione and GST-FKBP12 was exchanged 5× using a Centricon 10 filtration unit (Amicon) to remove the glutathione and exchange the buffer.

Molt 4 cells (1×10$^9$) were grown in standard media (RPMI 1640 containing 100 U/ml pennicillin, 100 ug/ml L-glutamine, 10% FCS). The cells were harvested and rinsed 3× with PBS (50 mM phosphate buffer, pH 7.0, 150 mM NaCl), flash frozen in dry-ice ethanol bath and stored at −80° C. On ice, the cells were thawed and lysed using a dounce homogenizer with B pestle in 5 ml of buffer A (10 mM Hepes, pH 7.5, 20 mM KCl, 1 mM EDTA, 0.4 mM PMSF and 2 mM 2-ME). After the debris was cleared by centrifugation at 1600 g for 10 min. and the membrane fraction was concentrated by 100,000 g centrifugation (1 hour), the 100,000 g pellet was incubated in 3 ml buffer B (50 mM Tris, pH 7.2, 100 mM NaCl, 20 mM KCl 0.2 mM PMSF, 1 mM 2-ME, 2 mM CaCl$_2$, 2 mM MgCl$_2$, 5 µg/ml aprotinin, leupeptin, pepstatin A and antipain), containing 12 mM CHAPSO for two hours at 4° C. The solubilized membrane proteins were separated from the debris by a 100,000 g centrifugation. After preabsorption of the supernatant for 3–18 hours with 0.4 ml glutathione sepharose resin swollen in buffer B, the supernatant was incubated with complexed Rapamycin-GST-FKBP12 (preformed by incubation of 660 ug GST-FKBP+60 ug RAPA in buffer B for 1–2 hours, 4° C.) for two hours at 4° C. The supernatant was then incubated for 2 hours at 4° C. with 100 ul glutathione resin (1:1 Buffer B). Nonspecific proteins were rinsed 5× with buffer C (buffer B+0.1% Triton×100) and the proteins eluted from the resin in Laemli buffer by incubation at 95° C. for 3 minutes and microcentrifugation. The proteins were separated by size using a 7% SDS-PAGE followed by silver stain. Four bands corresponding to proteins of molecular weights of 210 kDa, 208 kDa, 148 kDa, and 125 kDa were present in higher concentrations in the sample containing RAPA+GST-FKBP12 vs GST-FKBP alone.

The mitogen-stimulated thymocyte proliferation assay called the LAF, can be inhibited by rapamycin or analogs such as demethoxyrapamycin and indicates relative activity of Tapamycin analogs in immunosuppression. The same proteins were isolated using GST-FKBP complexed with the immunosuppressive analog, demethoxyrapamycin (Table 1). The Diels Alder adducts bound to FKBP12 and inhibited PPIase activity of FKBP12 but did not exhibit detectable immunosuppressive activity and thus do not bind to the target of rapamycin. The use of these two compounds complexed with GST-FKBP12 in the analogous isolation procedure (ie. replacing rapamycin:GST-FKBP12) yielded background levels of the 210 kDa proteins (no rapamycin) (Table 1). FK506, is an immunosuppressive compound which binds to FKBP and and mediates at least some of its effects through the binding of the FK506-FKBP complex with calcineurin. FK506 when complexed with GST-FKBP in an analogous procedure yielded only background levels of the 210 kDa protein (Table 1).

TABLE 1

Comparison of Binding of Rapamycin Analog--FKBP12 complexes to 210 kDa Protein

| Compound | 210 kDa | LAF | PPlase (Ki) |
| --- | --- | --- | --- |
| RAPA | +++ | 6 nM | 0.12 nM |
| demethoxyrapamycin | +++ | 58 nM | 4.4 nM |
| Diels Alder adduct (phenyl) | ± | >1000 nM | 12 nM |
| Diels Alder adduct (methyl) | ± | >1000 nM | 12 nM |
| FK506 | ± | 3 nM* | 0.4 nM |
| none (FKBP) | ± | | |

(*mechanism of action is different)

It is known that rapamycin must bind to a member of the FKBP family in order to mediate its effects. To verify that the proteins of this invention bind to the complex RAPA-GST-FKBP and not individually to rapamycin or FKBP12, a modified isolation procedure was employed. The modification consists of using (1) a rapamycin-42-biotin glycinate ester in place of rapamycin (both exhibit equivalent immunosuppressive activity in the LAF assay), (2) no exogenous FKBP and (3) a strepatavidin-conjugated resin in place of glutathione-resin. Only background levels of the 210 kDa protein was isolated using this modified isolation procedure.

The 210 kDa protein was isolated using the GST-FKBP12-rapamycin complex from BJAB cells (B cell lymphoma) and normal human T lymphocytes purified by Ficoll-Hypaque and T cell columns.

The results of the partial amino acid composition analysis are set forth in Table 2, below. It should be noted that the percentage of the basic amino acids was not determined.

TABLE 2

| Peak Number | Component Name | Retention Time | Peak Area | Response Factor | Peak Height | Concentration No./50 µl |
|---|---|---|---|---|---|---|
|  |  | 9.38 |  |  |  |  |
|  |  | 11.09 |  |  |  |  |
| 1 | Asp/Asn | 12.06 | 12.47076 | 0.02344 | 0.05142 | 0.30 |
| 2 | Thr | 13.05 | 2.92898 | 0.00000 | 0.00985 | 0.068 |
| 3 | Ser | 13.78 | 6.43968 | 0.00000 | 0.01995 | 0.15 |
|  |  | 15.68 |  |  |  |  |
| 4 | Glu/Gln | 16.87 | 25.47273 | 0.00000 | 0.05285 | 0.59 |
|  | Prp | 18.24 |  |  |  | 0.14 |
| 5 | Gly | 22.35 | 21.50384 | 0.00000 | 0.04645 | 0.44 |
|  |  | 22.90 |  |  |  |  |
| 6 | Ala | 23.73 | 16.69160 | 0.00000 | 0.03113 | 0.36 |
|  |  | 26.06 |  |  |  |  |
|  |  | 28.81 |  |  |  |  |
| 7 | Val | 29.39 | 4.83196 | 0.00000 | 0.00605 | 0.11 |
|  | Met | 32.28 |  |  |  |  |
| 8 | Ile | 34.10 | 3.00560 | 0.2326 | 0.00782 | 0.0699 |
| 9 | Leu | 35.09 | 5.73202 | 0.02331 | 0.01372 | 0.1383 |
| 10 | nLeu | 36.27 | 20.48232 | 0.02174 | 0.04286 | 0.4453 |
| 11 | Tyr | 38.33 | 1.44792 | 0.02618 | 0.00226 | 0.0379 |
| 12 | Phe | 40.05 | 1.25017 | 0.02703 | 0.00187 | 0.0338 |
| 13 | His | 47.79 | 1.50905 | 0.02553 | 0.00580 | 0.0385 |
| 14 |  | 51.80 | 12.66136 | 0.00000 | 0.01960 | 0.0000 |
| 15 | Lys | 53.34 | 9.90767 | 0.02283 | 0.02274 | 0.2262 |
| Totals |  |  | 146.53645 |  | 0.33436 |  |
| Not Determined |  |  | 144.29 |  |  |  |

EXAMPLE 2

The 210 kDa (210±20 kDa) protein of this invention was isolated from 4×10$^{11}$ Molt 4 cells using the affinity matrix protocol as described previously. Bound proteins were eluted from the affinity matrix with 1×Laemli buffer without glycerol and dye (0.0625 M Tris-HCl, ph6.8, 2% SDS, 0.37M b-mercaptoethanol) and were concentrated 3 consecutive times by centrifugation using centricon 100 (Amicon, Beverly, Mass.) at 4° C. the first two times and at 18° C. the third time. The concentrated sample was eluted from the centricon 100 filter by incubating 2 hours at room temperature with an equal volume of 2×laemli buffer without glycerol and dye the first 2× and 2×laemli buffer the third time. The proteins in the sample were separated by PAGE on a 1.5 mm thick 7% polyacrylamide gel (38.1). The proteins were transferred to polyvinylidine difluoride, PVDF, (Biorad, Hercules, Calif.) in 10×Tris/glycine buffer (Biorad) containing 0.037% SDS at 50 mAmps at 4° C. overnight. The proteins on the PVDP were stained with amido black (Biorad) in 10% ethanol, 2% acetic acid and the appropriate band was excised, rinsed with PBS and water and stored frozen.

Sequencing

The protein (approx. 3 ug) on the PVDF membrane was digested in situ with trypsin using a modification described by J. Fernandez et al, (Anal.Biochem. 201: 255–64, 1992).

Briefly, the PVDF was cut into 1 mm$^2$ pieces, prewet, and the protein digested in a 100 mM Tris-HCl, pH buffer containing 10% acetonitrile, and 1% reduced triton (CalBiochem) with 0.2 ug trypsin at 37° C. for 6 hours followed by addition of 0.2 ug trypsin and incubation overnight. The fragments were eluted from the membrane by sonication and the buffer containing the fragments were separated by microfuge centifugation. The membranes were backextracted 2× (i.e., 50 ul buffer was added to membranes, sonicated, and centrifuged in a microfuge and solution pooled with the original buffer containing the eluted fragments.) The sample (140–145 ul) was separated by narrow bore high performance liquid chromatography using a Vydac C18 2.1 mm×150 mm reverse phase column on a Hewlett Packard HPLC 1090 with a 40 diode array detector as described previously by W. Lane et al, (J.Protein Chem., 10(2): 151–60, 1991). Multiple fractions were collected and measured for absorption at multiple wavelengths (210, 277 and 292 nm). Optimal fractions were chosen for sequencing based on resolution, symmetry, and ultraviolet absorption and spectra (210 nm, 277 nm and 292 nm). An aliquot (5%) of the optimal fractions was analyzed for homogeneity and length of fragment by matrix assisted laser desorption time of flight mass spectrometry, MALDE-TOF-MS, on a Finnigan lasermat. Selected optimal fractions were sequenced by automated Edman degradation on an Applied Biosystems 477A protein sequencer using microcartridge and manufacturer's recommended chemistry cycle.

Sequence Comparison

Comparison was performed using the Intelligenetics suite (Intelligenetics, CA).

Sequences

Utilizing the methods mentioned above, it was determined that the 210 kDa (210±20 kDa) protein of this invention contains peptide fragments, four of which have amino acid sequences as shown below:

a) ILLNIEHR SEQ ID NO:5;
B) LIRPYMEPILK SEQ ID NO:6;
c) DXMEAQE SEQ ID NO:7; and
d) QLDHPLPTVTHPQVTYAYM(K) SEQ ID NO:8

Those skilled in the art will recognize the one-letter symbols for the amino acids in question (the definitions for which can also be seen at page 21 of the text *Biochemistry*, Third Edition, W. H. Freeman and Company, © 1988 by Lubert Stryer). Those so skilled will also understand that the X in sequence c) indicates an as yet unidentified amino acid and the parentheses in sequence d) indicates that the amino acid in the position in question is possibly lysine.

As mentioned previously, the present invention includes fragmented or truncated forms of the proteins mentioned herein. This includes proteins which have as part or all of their amino acid sequence one or more of the four sequences listed as a)–d), above. For the purposes of the claims, below, the proteins referred to as including one or more of the "internal amino acid sequences" are understood to be any protein which contains one of the sequences listed above, whether the protein is comprised wholly of one or more of the sequences a)–d) or whether one or more of the sequences mentioned above form any portion of the protein. This is understood to include all locations on the protein's amino acid sequence including, but not limited to, those sections of the protein which initiate and terminate the protein's amino acid chain.

These partial amino acid sequences were compared with sequences in the Genbank database. There was identity with the sequence, accession number L34075 (Brown et al., Nature 369, 756–758 (1994)). The cDNA of the SEP gene was cloned as follows: Two micrograms of Molt 4 cDNA (Clontech, Palo Alto, Calif.) in 1× PCR buffer (10 mM Tris-HCl, pH 8.3, 50 mM KCl, 1 mM MgCl, 200 μM dDATP, 200 μM dTTP, 200 μM dCTP, 200 μM dGTP; Perkin Elmer,) with 1 unit Taq polymerase (Perlin Elmer), was amplified by Polymerase chain reaction (PCR) at 94 C. for 30 sec., 66 C. for 4 min for 30 cycles, 72 C. for 10 min by three separate reactions containing one of the following pairs of oligomers:

CGATCGGTCGACTGCAGCACTTTGGG-GATTGTGCTCTC SEQ ID NO:9 and
GCGGCCGCAGCTTTCTTCATGCATGA-CAACAGCCCAGGC SEQ ID NO:10; or
GCGGCCGCAAGCTTCAAGTATGCAAGC-CTGTGCGGCAAGA SEQ ID NO:11 and
CGATCGGTCGACACCTTCTGCATCA-GAGTCAAGTGGTCA SEQ ID NO:12; or
GCGGCCGCAAGCTTCCTCAGCTCACATC-CTTAGAGCTGCA SEQ ID NO:13 and
CGATCGGTCGACTTATTACCA-GAAAGGGCACCAGCCAATATA SEQ ID NO:14.

The oligonucleotides were synthesized and isolated by methods previously described and known in the art (Chemical and Enzymatic Synthesis of Gene Fragments, ed. by H. G. Gassin and Anne Lang, Verlag Chemie, FLA, 1982). The resulting PCR products named SEP3, SEP4, and SEP5, respectively, were incubated at 15 C. overnight in buffer containing T4 DNA ligase (1 unit) and 50 ng pcII which was modified to efficiently ligate PCR products (TA cloning kit, Invitrogen, San Diego, Calif.) to yield PCR-pcII ligated products. The PCR-pcII products were transformed into competent E. coli INValphaF cells obtained commercially from Invitrogen. Miniprep DNA was prepared using the Quiagen miniprep kits (Quiagen, Chatsworth, Calif.) and the clones containing the appropriate sized PCR product were identified by restriction enzyme digestion with commercially available HindIII or Sal I, electrophoresis, and comparison to standards. Sep2 and Sep1 cDNA was made using the TimeSaver cDNA synthesis Kit (Pharmacia, Piscataway, N.J.) with the first strand synthesis reaction containing oligodT (0.13 μg) and 250 pmoles of
CGATCGGTCGACCAGATGAGCACATCAT-AGCGCTGATGA SEQ ID NO:15 or
CGATCGGTCGACAAATTCAAAGCTGC-CAAGCGTTCGGAG SEQ ID NO:16,
respectively. Sep2 and Sep1 second strand synthesis was performed using the TimeSaver cDNA synthesis kit with the addition of 250 pmoles of
GCGGCCGCAAGCTTTGGCTCGAG-CAATGGGGCCAGGCA SEQ ID NO:17 or
GCGGCCGCAAGCTTAAGATGCTTGGAAC-CGCACCTGCCG SEQ ID NO:18,
respectively. The Sep2 and Sep1 cDNA was then amplified by PCR using
CGATCGGTCGACCAGATGAGCACATCAT-AGCGCTGATGA SEQ ID NO:19 and
GCGGCCGCAAGCTTTGGCTCGAG-CAATGGGGCCAGGCA SEQ ID NO:20 or
GCGGCCGCAAGCTTAAGATGCTTGGAAC-CGCACCTGCCG SEQ ID NO:21 and
CGATCGGTCGACAAATTCAAAGCTGC-CAAGCGTTCGGAG SEQ ID NO:22,
respectively as described above. The Sep2 PCR products were cloned into pcII using the TA cloning kit (Invitrogen). The Sep 1 PCR products were digested with Hind III and Sal I, separated from the pcII vector by agarose electrophoresis. The Sep1 (HindIII-SalI) fragment was isolated using the Sephaglas bandprep kit from Pharmacia and cloned into the HindIII and Sal I sites of pUC19 as described (Sambrook et al., Molecular Cloning Cold Spring Harbor, 1989). Ligation of the isolated Sep2(HindIII, AspI) and Sep3(AspI, SalI) fragments or Sep4(HindIII, AccIII/MroI) and Sep5(AccIII/MroI, Sal I) fragments into pUC18(HindIII, SalI) vector and transformation of competent E. coli INValphaF cells (Invitrogen) was performed by techniques known to those skilled in the art (Sambrook et al., Molecular Cloning Cold Spring Harbor, 1989) to obtain pUC18-Sep 23 and pUC18-Sep45 which contain nucleotides 1468–5326 and 4964–7653, respectively, of the full length clone shown in the attached Sequence No. 1. Ligation of the pUC19-Sep1 (EcoRV, SalI), Sep2345 (EcoRV, SalI) fragments and transformation of competent E. coli INValphaF cells (Invitrogen) were performed by techniques known to those skilled in the art (as described by Sambrook et al., Molecular Cloning Cold Spring Harbor, 1989) to obtain the full length clone. The nucleic acid sequence coding for this protein and its amino acid sequence are shown in Sequence No. 1.

A fusion protein, called glutathione S transferase-sirolimus effect or protein, GST-SEP, was engineered by subcloning the Sep4 and Sep5 fragments into the plasmid, pGEX-KG (Guan, K. and Dixon, J. E. (1991) Anal. Biochem. 192, 262–267) as follows. Briefly, Sep4 was digested with commercially available HindIII restriction enzyme, the restriction site was filled in with the Klenow fragment of DNA polymerase (Gibco), and the DNA was extracted with phenol-chloroform and ethanol precipitated using techniques known by those skilled in the art (Sambrook et al., Molecular Cloning Cold Spring Harbor, 1989). The SEP4 (HindIII-Klenow) was further digested with MroI restriction enzyme, separated from the pcII vector by agarose electrophoresis and isolated as the fragment SEP4-Hindlll-Klenow-MroI. Sep5 fragment was prepared by digestion with SalI and MroI, separated from the pcII vector by agarose electrophoresis and isolated as the fragment SEP5-SalI-MroI. pGEX-KG (Guan, K. and Dixon, J. E. (1991) Anal. Biochem. 192, 262–267) was digested with Nco I, filled in with the Klenow fragment of DNA polymerase and the DNA was extracted with phenol-chloroform and ethanol precipitated, using techniques of those skilled in the art (Sambrook et al., Molecular Cloning Cold Spring Harbor, 1989). pGEX-KG (NcoI, Klenow) was further digested with Sal I, separated from the undigested vector by agarose electrophoresis and isolated as the vector pGEX-KG-NcoI-Klenow-SalI, using techniques of those skilled in the art. Ligation of the vector, pGEX-KG-Ncol-Klenow-SalI and Sep 4 (HindIII, MroI) and Sep5 (MroI, SalI) fragments and transformation into E. coli strain INValphaF cells (Invitrogen) using techniques of those skilled in the art yielded the plasmid, pGEX-Sep45. Other E. coli hosts such as BL21 can also be used The DNA and protein sequence of this fusion protein is shown in Sequence No. 2.

Flag sequences and kinase recognition domain of heart muscle kinase can be added at the amino terminal end, by methods known in the art (see Chen et al., Gene Feb. 11, 1994; 139 (1): 73–75) within SEP or at the carboxy terminus of SEP, SEP4,5 or other fragments using an oligonucleotide which includes the coding sequence for Asp Tyr Lys Asp Asp Asp Asp Lys SEQ ID NO:23. The fusion protein can be isolated by affinity chromatography with anti-flag specific antibodies using the commercially available kits from IBI, New Haven, Conn.

Transformed host cells containing sequences of this invention have been deposited with the American Type Culture Collection (ATCC), 12301 Parklawn Drive, Rockville, Md. 20852, USA, and have been given the ATCC designations listed below:

| | Sequence | ATCC Designation |
|---|---|---|
| a) | pUC19-Sep1(nucleotides 1–1785 of Sequence No. 1) | ATCC 69756 |
| b) | pUC18-Sep23 (nucleotides 1468–5326 of Sequence No. 1) | ATCC 69753 |
| c) | pUC18-Sep45 (nucleotides 4964–7653 of Sequence No. 1) | ATCC 69754 |
| d) | pUC19-Sep1-5 (ATCC 69756 1–7653 of sequence 1) | ATCC 69829 |
| e) | pGEX-Sep45 plasmids (Sequence 2) | ATCC 69755. |

EXAMPLE 3

The 210 kDa protein of this invention was also isolated by the techniques described in Example 1 utilizing the following rapamycin analogs:

a) 42-Deoxy-42-[1-(1,1-dimethylethoxy)-2-oxoethoxy] rapamycin (which is described in U.S. Pat. No. 5,233,036);

b) 42-[O-[(1,1-Dimethylethyl)dimethylsilyl]]rapamycin (described in U.S. Pat. No. 5,120,842);

c) Rapamycin 42-ester with N-[1,1-dimethylethoxy) carbonyl]-N-methylglycine (described in U.S. Pat. No. 5,130,307);

d) Rapamycin 42-ester with 5-(1,1-dimnethylethoxy)-2-[[(1,1-dimethylethoxy)carbonyl]amino]-5-oxopentanoic acid ethyl acetate solvate three quarter hydrate (see U.S. Pat. No. 5,130,307);

e) Rapamycin 42-ester with N-[(1,1-dimethylethoxy) carbonyl]glycylglycine hydrate (see U.S. Pat. No. 5,130,307); and f) Rapamycin 42-ester with N2, N6-bis[(1,1-dimethylethoxy)carbonyl]-L-lysine (see U.S. Pat. No. 5,130,307).

What is claimed:

1. An isolated polypepbide having a molecular weight of about 210 kDa as determined by SDS-PAGE, the polypeptide made by a process comprising the steps of:

(a) providing a sample of human cellular material;

(b) preparing an extract of the cellular material comprising cell membrane proteins, (c) contacting the extrct with an affinity reagent comprising a complex of:
  (i) rapamycin, and
  (ii) FKBP12 under conditions which permit materials capable of specifically binding to the affinity reagent to bind thereto;

(d) separating materials which do not bind to the affinity reagent from the affinity reagent and the materials bound thereto;

(e) dissociating the materials bound to the affinity reagent therefrom; and (f) separating the polypeptide having a molecular weight of about 210 kDa from the other materials dissociated from the affinity reagent.

2. An isolated rapamycin effector protein having a molecular weight of about 210 kDa, wherein said rapamycin effector protein is a rapamycin effector protein which can be obtained from a human, and wherein said rapamycin effector protein binds to a complex of:
  a) FKBP12 and
  b) rapamycin as determined by SDS-PAGE.

* * * * *

UNITED STATES PATENT AND TRADEMARK OFFICE
CERTIFICATE OF CORRECTION

PATENT NO. : 6,313,264 B1
DATED : November 6, 2001
INVENTOR(S) : Thomas J. Caggiano, Yanqiu Chen, Amedeo A. Failli, Katherine L. Molnar-Kimber and Koji Nakanishi It is certified that error appears in the above-identified patent and that said Letters Patent is hereby corrected as shown below:

<u>Column 53</u>,
Line 26, delete "polypepbide" and substitute therefor -- polypeptide --.
Line 34, delete "proteins," and substitute therefor -- proteins; --.
Line 35 delete "extrct" and substitute therefor -- extract --.

<u>Column 54</u>,
Line 35, delete "210 kDa," and substitute therefor -- 210 kDa as determined by SDS-PAGE, --.
Line 40, delete "as determined by SDS-PAGE".

Signed and Sealed this

Twenty-eighth Day of May, 2002

Attest:

*Attesting Officer*

JAMES E. ROGAN
*Director of the United States Patent and Trademark Office*

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
        (A) LENGTH: 7653 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:1:

```
AAGATGCTTG GAACCGGACC TGCCGCCGCC ACCACCGCTG CCACCACATC TAGCAATGTG      60

AGCGTCCTGC AGCAGTTTGC CAGTGGCCTA AAGAGCCGGA ATGAGGAAAC CAGGGCCAAA     120

GCCGCCAAGG AGCTCCAGCA CTATGTCACC ATGGAACTCC GAGAGATGAG TCAAGAGGAG     180

TCTACTCGCT TCTATGACCA ACTGAACCAT CACATTTTTG AATTGGTTTC CAGCTCAGAT     240

GCCAATGAGA GGAAAGGTGG CATCTTGGCC ATAGCTAGCC TCATAGGAGT GGAAGGTGGG     300

AATGCCACCC GAATTGGCAG ATTTGCCAAC TATCTTCGGA ACCTCCTCCC CTCCAATGAC     360

CCAGTTGTCA TGGAAATGGC ATCCAAGGCC ATTGGCCGTC TTGCCATGGC AGGGGACACT     420

TTTACCGCTG AGTACGTGGA ATTTGAGGTG AAGCGAGCCC TGGAATGGCT GGGTGCTGAC     480

CGCAATGAGG GCCGGAGACA TGCAGCTGTC CTGGTTCTCC GTGAGCTGGC CATCAGCGTC     540

CCTACCTTCT TCTTCCAGCA AGTGCAACCC TTCTTTGACA ACATTTTTGT GGCCGTGTGG     600

GACCCCAAAC AGGCCATCCG TGAGGGAGCT GTAGCCGCCC TTCGTGCCTG TCTGATTCTC     660

ACAACCCAGC GTGAGCCGAA GGAGATGCAG AAGCCTCAGT GGTACAGGCA CACATTTGAA     720

GAAGCAGAGA AGGGATTTGA TGAGACCTTG GCCAAAGAGA AGGGCATGAA TCGGGATGAT     780

CGGATCCATG GAGCCTTGTT GATCCTTAAC GAGCTGGTCC GAATCAGCAG CATGGAGGGA     840

GAGCGTCTGA GAGAAGAAAT GGAAGAAATC ACACAGCAGC AGCTGGTACA CGACAAGTAC     900

TGCAAAGATC TCATGGGCTT CGGAACAAAA CCTCGTCACA TTACCCCCTT CACCAGTTTC     960
```

-continued

| | | | | | |
|---|---|---|---|---|---|
| CAGGCTGTAC | AGCCCCAGCA | GTCAAATGCC | TTGGTGGGGC | TGCTGGGGTA | CAGCTCTCAC | 1020 |
| CAAGGCCTCA | TGGGATTTGG | GACCTCCCCC | AGTCCAGCTA | AGTCCACCCT | GGTGGAGAGC | 1080 |
| CGGTGTTGCA | GAGACTTGAT | GGAGGAGAAA | TTTGATCAGG | TGTGCCAGTG | GGTGCTGAAA | 1140 |
| TGCAGGAATA | GCAAGAACTC | GCTGATCCAA | ATGACAATCC | TTAATTTGTT | GCCCCGCTTG | 1200 |
| GCTGCATTCC | GACCTTCTGC | CTTCACAGAT | ACCCAGTATC | TCCAAGATAC | CATGAACCAT | 1260 |
| GCCCTAAGCT | GTGTCAAGAA | GGAGAAGGAA | CGTACAGCGG | CCTTCCAAGC | CCTGGGGCTA | 1320 |
| CTTTCTGTGG | CTGTGAGGTC | TGAGTTTAAG | GTCTATTTGC | CTCGCGTGCT | GGACATCATC | 1380 |
| CGAGCGGCCC | TGCCCCCAAA | GGACTTCGCC | CATAAGAGGC | AGAAGGCAAT | GCAGGTGGAC | 1440 |
| GCCACAGTCT | TCACTTGCAT | CAGCATGCTG | GCTCGAGCAA | TGGGGCCAGG | CATCCAGCAG | 1500 |
| GATATCAAGG | AGCTGCTGGA | GCCCATGCTG | GCAGTGGGAC | TAAGCCCTGC | CCTCACTGCA | 1560 |
| GTGCTCTACG | ACCTGAGCCG | TCAGATTCCA | CAGCTAAAGA | AGGACATTCA | AGATGGGCTA | 1620 |
| CTGAAAATGC | TGTCCCTGGT | CCTTATGCAC | AAACCCCTTC | GCCACCCAGG | CATGCCCAAG | 1680 |
| GGCCTGGCCC | ATCAGCTGGC | CTCTCCTGGC | CTCACGACCC | TCCCTGAGGC | CAGCGATGTG | 1740 |
| GGCAGCATCA | CTCTTGCCCT | CCGAACGCTT | GGCAGCTTTG | AATTTGAAGG | CCACTCTCTG | 1800 |
| ACCCAATTTG | TTCGCCACTG | TGCGGATCAT | TTCCTGAACA | GTGAGCACAA | GGAGATCCGC | 1860 |
| ATGGAGGCTG | CCCGCACCTG | CTCCCGCCTG | CTCACACCCT | CCATCCACCT | CATCAGTGGC | 1920 |
| CATGCTCATG | TGGTTAGCCA | GACCGCAGTG | CAAGTGGTGG | CAGATGTGCT | TAGCAAACTG | 1980 |
| CTCGTAGTTG | GGATAACAGA | TCCTGACCCT | GACATTCGCT | ACTGTGTCTT | GGCGTCCCTG | 2040 |
| GACGAGCGCT | TTGATGCACA | CCTGGCCCAG | GCGGAGAACT | GCAGGCCTT | GTTTGTGGCT | 2100 |
| CTGAATGACC | AGGTGTTTGA | GATCCGGGAG | CTGGCCATCT | GCACTGTGGG | CCGACTCAGT | 2160 |
| AGCATGAACC | CTGCCTTTGT | CATGCCTTTC | CTGCGCAAGA | TGCTCATCCA | GATTTTGACA | 2220 |
| GAGTTGGAGC | ACAGTGGGAT | TGGAAGAATC | AAAGAGCAGA | GTGCCCGCAT | GCTGGGGCAC | 2280 |
| CTGGTCTCCA | ATGCCCCCCG | ACTCATCCGC | CCCTACATGG | AGCCTATTCT | GAAGGCATTA | 2340 |
| ATTTTGAAAC | TGAAAGATCC | AGACCCTGAT | CCAAACCCAG | GTGTGATCAA | TAATGTCCTG | 2400 |
| GCAACAATAG | GAGAATTGGC | ACAGGTTAGT | GGCCTGGAAA | TGAGGAAATG | GGTTGATGAA | 2460 |
| CTTTTTATTA | TCATCATGGA | CATGCTCCAG | GATTCCTCTT | TGTTGGCCAA | AAGGCAGGTG | 2520 |
| GCTCTGTGGA | CCCTGGGACA | GTTGGTGGCC | AGCACTGGCT | ATGTAGTAGA | GCCCTACAGG | 2580 |
| AAGTACCCTA | CTTTGCTTGA | GGTGCTACTG | AATTTTCTGA | AGACTGAGCA | GAACCAGGGT | 2640 |
| ACACGCAGAG | AGGCCATCCG | TGTGTTAGGG | CTTTTAGGGG | CTTTGGATCC | TTACAAGCAC | 2700 |
| AAAGTGAACA | TTGGCATGAT | AGACCAGTCC | CGGGATGCCT | CTGCTGTCAG | CCTGTCAGAA | 2760 |
| TCCAAGTCAA | GTCAGGATTC | CTCTGACTAT | AGCACTAGTG | AAATGCTGGT | CAACATGGGA | 2820 |
| AACTTGCCTC | TGGATGAGTT | CTACCCAGCT | GTGTCCATGG | TGGCCCTGAT | GCGGATCTTC | 2880 |
| CGAGACCAGT | CACTCTCTCA | TCATCACACC | ATGGTTGTCC | AGGCCATCAC | CTTCATCTTC | 2940 |
| AAGTCCCTGG | GACTCAAATG | TGTGCAGTTC | CTGCCCCAGG | TCATGCCCAC | GTTCCTTAAT | 3000 |
| GTCATTCGAG | TCTGTGATGG | GGCCATCCGG | GAATTTTTGT | TCCAGCAGCT | GGGAATGTTG | 3060 |
| GTGTCCTTTG | TGAAGAGCCA | CATCAGACCT | TATATGGATG | AAATAGTCAC | CCTCATGAGA | 3120 |
| GAATTCTGGG | TCATGAACAC | CTCAATTCAG | AGCACGATCA | TTCTTCTCAT | TGAGCAAATT | 3180 |
| GTGGTAGCTC | TTGGGGGTGA | ATTTAAGCTC | TACCTGCCCC | AGCTGATCCC | ACACATGCTG | 3240 |
| CGTGTCTTCA | TGCATGACAA | CAGCCCAGGC | CGCATTGTCT | CTATCAAGTT | ACTGGCTGCA | 3300 |

-continued

```
ATCCAGCTGT TTGGCGCCAA CCTGGATGAC TACCTGCATT TACTGCTGCC TCCTATTGTT      3360

AAGTTGTTTG ATGCCCCTGA AGCTCCACTG CCATCTCGAA AGGCAGCGCT AGAGACTGTG      3420

GACCGCCTGA CGGAGTCCCT GGATTTCACT GACTATGCCT CCCGGATCAT TCACCCTATT      3480

GTTCGAACAC TGGACCAGAG CCCAGAACTG CGCTCCACAG CCATGGACAC GCTGTCTTCA      3540

CTTGTTTTTC AGCTGGGGAA GAAGTACCAA ATTTTCATTC AATGGTGAA  TAAAGTTCTG      3600

GTGCGACACC GAATCAATCA TCAGCGCTAT GATGTGCTCA TCTGCAGAAT TGTCAAGGGA      3660

TACACACTTG CTGATGAAGA GGAGGATCCT TTGATTTACC AGCATCGGAT GCTTAGGAGT      3720

GGCCAAGGGG ATGCATTGGC TAGTGGACCA GTGGAAACAG GACCCATGAA GAAACTGCAC      3780

GTCAGCACCA TCAACCTCCA AAAGGCCTGG GGCGCTGCCA GGAGGGTCTC CAAAGATGAC      3840

TGGCTGGAAT GGCTGAGACG GCTGAGCCTG GAGCTGCTGA AGGACTCATC ATCGCCCTCC      3900

CTGCGCTCCT GCTGGGCCCT GGCACAGGCC TACAACCCGA TGGCCAGGGA TCTCTTCAAT      3960

GCTGCATTTG TGTCCTGCTG GTCTGAACTG AATGAAGATC AACAGGATGA GCTCATCAGA      4020

AGCATCGAGT TGGCCCTCAC CTCACAAGAC ATCGCTGAAG TCACACAGAC CCTCTTAAAC      4080

TTGGCTGAAT TCATGGAACA CAGTGACAAG GGCCCCCTGC CACTGAGAGA TGACAATGGC      4140

ATTGTTCTGC TGGGTGAGAG AGCTGCCAAG TGCCAGCAT  ATGCCAAAGC ACTACACTAC      4200

AAAGAACTGG AGTTCCAGAA AGGCCCCACC CCTGCCATTC TAGAATCTCT CATCAGCATT      4260

AATAATAAGC TACAGCAGCC GGAGGCAGCG GCCGGAGTGT TAGAATATGC CATGAAACAC      4320

TTTGGAGAGC TGGAGATCCA GGCTACCTGG TATGAGAAAC TGCACGAGTG GGAGGATGCC      4380

CTTGTGGCCT ATGACAAGAA AATGGACACC AACAAGGACG ACCCAGAGCT GATGCTGGGC      4440

CGCATGCGCT GCCTCGAGGC CTTGGGGGAA TGGGGTCAAC TCCACCAGCA GTGCTGTGAA      4500

AAGTGGACCC TGGTTAATGA TGAGACCCAA GCCAAGATGG CCCGGATGGC TGCTGCAGCT      4560

GCATGGGGTT TAGGTCAGTG GGACAGCATG GAAGAATACA CCTGTATGAT CCCTCGGGAC      4620

ACCCATGATG GGCATTTTA  TAGAGCTGTG CTGGCACTGC ATCAGGACCT CTTCTCCTTG      4680

GCACAACAGT GCATTGACAA GGCCAGGGAC CTGCTGGATG CTGAATTAAC TGCAATGGCA      4740

GGAGAGAGTT ACAGTCGGGC ATATGGGCC  ATGGTTTCTT GCCACATGCT GTCCGAGCTG      4800

GAGGAGGTTA TCCAGTACAA ACTTGTCCCC GAGCGACGAG AGATCATCCG CCAGATCTGG      4860

TGGGAGAGAC TGCAGGGCTG CCAGCGTATC GTAGAGGACT GGCAGAAAAT CCTTATGGTG      4920

CGGTCCCTTG TGGTCAGCCC TCATGAAGAC ATGAGAACCT GGCTCAAGTA TGCAAGCCTG      4980

TGCGGCAAGA GTGGCAGGCT GGCTCTTGCT CATAAAACTT TAGTGTTGCT CCTGGGAGTT      5040

GATCCGTCTC GGCAACTTGA CCATCCTCTG CCAACAGTTC ACCCTCAGGT GACCTATGCC      5100

TACATGAAAA ACATGTGGAA GAGTGCCCGC AAGATCGATG CCTTCCAGCA CATGCAGCAT      5160

TTTGTCCAGA CCATGCAGCA ACAGGCCCAG CATGCCATCG CTACTGAGGA CCAGCAGCAT      5220

AAGCAGGAAC TGCACAAGCT CATGGCCCGA TGCTTCCTGA AACTTGGAGA GTGGCAGCTG      5280

AATCTACAGG GCATCAATGA GAGCACAATC CCCAAAGTGC TGCAGTACTA CAGCGCCGCC      5340

ACAGAGCACG ACCGCAGCTG GTACAAGGCC TGGCATGCGT GGGCAGTGAT GAACTTCGAA      5400

GCTGTGCTAC ACTACAAACA TCAGAACCAA GCCCGCGATG AGAAGAAGAA ACTGCGTCAT      5460

GCCAGCGGGG CCAACATCAC CAACGCCACC ACTGCCGCCA CCACGGCCGC CACTGCCACC      5520

ACCACTGCCA GCACCGAGGG CAGCAACAGT GAGAGCGAGG CCGAGAGCAC CGAGAACAGC      5580

CCCACCCCAT CGCCGCTGCA GAAGAAGGTC ACTGAGGATC TGTCCAAAAC CCTCCTGATG      5640

TACACGGTGC CTGCCGTCCA GGGCTTCTTC CGTTCCATCT CCTTGTCACG AGGCAACAAC      5700
```

-continued

```
CTCCAGGATA CACTCAGAGT TCTCACCTTA TGGTTTGATT ATGGTCACTG GCCAGATGTC    5760

AATGAGGCCT TAGTGGAGGG GGTGAAAGCC ATCCAGATTG ATACCTGGCT ACAGGTTATA    5820

CCTCAGCTCA TTGCAAGAAT TGATACGCCC AGACCCTTGG TGGGACGTCT CATTCACCAG    5880

CTTCTCACAG ACATTGGTCG GTACCACCCC CAGGCCCTCA TCTACCCACT GACAGTGGCT    5940

TCTAAGTCTA CCACGACAGC CCGGCACAAT GCAGCCAACA AGATTCTGAA GAACATGTGT    6000

GAGCACAGCA ACACCCTGGT CCAGCAGGCC ATGATGGTGA GCGAGGAGCT GATCCGAGTG    6060

GCCATCCTCT GGCATGAGAT GTGGCATGAA GGCCTGGAAG AGGCATCTCG TTTGTACTTT    6120

GGGGAAAGGA ACGTGAAAGG CATGTTTGAG GTGCTGGAGC CCTTGCATGC TATGATGGAA    6180

CGGGGCCCCC AGACTCTGAA GGAAACATCC TTTAATCAGG CCTATGGTCG AGATTTAATG    6240

GAGGCCCAAG AGTGGTGCAG GAAGTACATG AAATCAGGGA ATGTCAAGGA CCTCACCCAA    6300

GCCTGGGACC TCTATTATCA TGTGTTCCGA CGAATCTCAA AGCAGCTGCC TCAGCTCACA    6360

TCCTTAGAGC TGCAATATGT TTCCCCAAAA CTTCTGATGT GCCGGGACCT TGAATTGGCT    6420

GTGCCAGGAA CATATGACCC CAACCAGCCA ATCATTCGCA TTCAGTCCAT AGCACCGTCT    6480

TTGCAAGTCA TCACATCCAA GCAGAGGCCC CGGAAATTGA CACTTATGGG CAGCAACGGA    6540

CATGAGTTTG TTTTCCTTCT AAAAGGCCAT GAAGATCTGC GCCAGGATGA GCGTGTGATG    6600

CAGCTCTTCG GCCTGGTTAA CACCCTTCTG GCCAATGACC CAACATCTCT TCGGAAAAAC    6660

CTCAGCATCC AGAGATACGC TGTCATCCCT TTATCGACCA ACTCGGGCCT CATTGGCTGG    6720

GTTCCCCACT GTGACACACT GCACGCCCTC ATCCGGGACT ACAGGGAGAA GAAGAAGATC    6780

CTTCTCAACA TCGAGCATCG CATCATGTTG CGGATGGCTC CGGACTATGA CCACTTGACT    6840

CTGATGCAGA AGGTGGAGGT GTTTGAGCAT GCCGTCAATA ATACAGCTGG GGACGACCTG    6900

GCCAAGCTGC TGTGGCTGAA AAGCCCCAGC TCCGAGGTGT GGTTTGACCG AAGAACCAAT    6960

TATACCCGTT CTTTAGCGGT CATGTCAATG GTTGGGTATA TTTTAGGCCT GGGAGATAGA    7020

CACCCATCCA ACCTGATGCT GGACCGTCTG AGTGGGAAGA TCCTGCACAT TGACTTTGGG    7080

GACTGCTTTG AGGTTGCTAT GACCCGAGAG AAGTTTCCAG AGAAGATTCC ATTTAGACTA    7140

ACAAGAATGT TGACCAATGC TATGGAGGTT ACAGGCCTGG ATGGCAACTA CAGAATCACA    7200

TGCCACACAG TGATGGAGGT GCTGCGAGAG CACAAGGACA GTGTCATGGC CGTGCTGGAA    7260

GCCTTTGTCT ATGACCCCTT GCTGAACTGG AGGCTGATGG ACACAAATAC CAAAGGCAAC    7320

AAGCGATCCC GAACGAGGAC GGATTCCTAC TCTGCTGGCC AGTCAGTCGA AATTTTGGAC    7380

GGTGTGGAAC TTGGAGAGCC AGCCCATAAG AAAACGGGGA CCACAGTGCC AGAATCTATT    7440

CATTCTTTCA TTGGAGACGG TTTGGTGAAA CCAGAGGCCC TAAATAAGAA AGCTATCCAG    7500

ATTATTAACA GGGTTCGAGA TAAGCTCACT GGTCGGGACT TCTCTCATGA TGACACTTTG    7560

GATGTTCCAA CGCAAGTTGA GCTGCTCATC AAACAAGCGA CATCCCATGA AAACCTCTGC    7620

CAGTGCTATA TTGGCTGGTA CCCTTTCTGG TAA                                 7653
```

(2) INFORMATION FOR SEQ ID NO:2:

(i) SEQUENCE CHARACTERISTICS:
        (A) LENGTH: 3423 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:2:

```
ATGTCCCCTA TACTAGGTTA TTGGAAAATT AAGGGCCTTG TGCAACCCAC TCGACTTCTT      60
TTGGAATATC TTGAAGAAAA ATATGAAGAG CATTTGTATG AGCGCGATGA AGGTGATAAA     120
TGGCGAAACA AAAAGTTTGA ATTGGGTTTG GAGTTTCCCA ATCTTCCTTA TTATATTGAT     180
GGTGATGTTA AATTAACACA GTCTATGGCC ATCATACGTT ATATAGCTGA CAAGCACAAC     240
ATGTTGGGTG GTTGTCCAAA AGAGCGTGCA GAGATTTCAA TGCTTGAAGG AGCGGTTTTG     300
GATATTAGAT ACGGTGTTTC GAGAATTGCA TATAGTAAAG ACTTTGAAAC TCTCAAAGTT     360
GATTTTCTTA GCAAGCTACC TGAAATGCTG AAAATGTTCG AAGATCGTTT ATGTCATAAA     420
ACATATTTAA ATGGTGATCA TGTAACCCAT CCTGACTTCA TGTTGTATGA CGCTCTTGAT     480
GTTGTTTTAT ACATGGACCC AATGTGCCTG GATGCGTTCC CAAAATTAGT TTGTTTTAAA     540
AAACGTATTG AAGCTATCCC ACAAATTGAT AAGTACTTGA ATCCAGCAA GTATATAGCA      600
TGGCCTTTGC AGGGCTGGCA AGCCACGTTT GGTGGTGGCG ACCATCCTCC AAAATCGGAT     660
CTGGTTCCGC GTGGTGGATC CCCGGGAATT TCCGGTGGTG GTGGTGGTGG AATTCTAGAC     720
GACTCCATGA GCTTCAAGTA TGCAAGCCTG TGCGGCAAGA GTGGCAGGCT GGCTCTTGCT     780
CATAAAACTT TAGTGTTGCT CCTGGGAGTT GATCCGTCTC GGCAACTTGA CCATCCTCTG     840
CCAACAGTTC ACCCTCAGGT GACCTATGCC TACATGAAAA ACATGTGGAA GAGTGCCCGC     900
AAGATCGATG CCTTCCAGCA CATGCAGCAT TTTGTCCAGA CCATGCAGCA ACAGGCCCAG     960
CATGCCATCG CTACTGAGGA CCAGCAGCAT AAGCAGGAAC TGCACAAGCT CATGGCCCGA    1020
TGCTTCCTGA AACTTGGAGA GTGGCAGCTG AATCTACAGG GCATCAATGA GAGCACAATC    1080
CCCAAAGTGC TGCAGTACTA CAGCGCCGCC ACAGAGCACG ACCGCAGCTG GTACAAGGCC    1140
TGGCATGCGT GGGCAGTGAT GAACTTCGAA GCTGTGCTAC ACTACAAACA TCAGAACCAA    1200
GCCCGCGATG AGAAGAAGAA ACTGCGTCAT GCCAGCGGGG CCAACATCAC CAACGCCACC    1260
ACTGCCGCCA CCACGGCCGC CACTGCCACC ACCACTGCCA GCACCGAGGG CAGCAACAGT    1320
GAGAGCGAGG CCGAGAGCAC CGAGAACAGC CCCACCCCAT CGCCGCTGCA GAAGAAGGTC    1380
ACTGAGGATC TGTCCAAAAC CCTCCTGATG TACACGGTGC CTGCCGTCCA GGGCTTCTTC    1440
CGTTCCATCT CCTTGTCACG AGGCAACAAC CTCCAGGATA CACTCAGAGT TCTCACCTTA    1500
TGGTTTGATT ATGGTCACTG GCCAGATGTC AATGAGGCCT TAGTGGAGGG GGTGAAAGCC    1560
ATCCAGATTG ATACCTGGCT ACAGGTTATA CCTCAGCTCA TTGCAAGAAT TGATACGCCC    1620
AGACCCTTGG TGGGACGTCT CATTCACCAG CTTCTCACAG ACATTGGTCG GTACCACCCC    1680
CAGGCCCTCA TCTACCCACT GACAGTGGCT TCTAAGTCTA CCACGACAGC CCGGCACAAT    1740
GCAGCCAACA AGATTCTGAA GAACATGTGT GAGCACAGCA ACACCCTGGT CCAGCAGGCC    1800
ATGATGGTGA GCGAGGAGCT GATCCGAGTG GCCATCCTCT GGCATGAGAT GTGGCATGAA    1860
GGCCTGGAAG AGGCATCTCG TTTGTACTTT GGGGAAAGGA ACGTGAAAGG CATGTTTGAG    1920
GTGCTGGAGC CCTTGCATGC TATGATGGAA CGGGGCCCCC AGACTCTGAA GGAAACATCC    1980
TTTAATCAGG CCTATGGTCG AGATTTAATG GAGGCCCAAG AGTGGTGCAG GAAGTACATG    2040
AAATCAGGGA ATGTCAAGGA CCTCACCCAA GCCTGGGACC TCTATTATCA TGTGTTCCGA    2100
CGAATCTCAA AGCAGCTGCC TCAGCTCACA TCCTTAGAGC TGCAATATGT TTCCCCAAAA    2160
CTTCTGATGT GCCGGGACCT TGAATTGGCT GTGCCAGGAA CATATGACCC CAACCAGCCA    2220
ATCATTCGCA TTCAGTCCAT AGCACCGTCT TTGCAAGTCA TCACATCCAA GCAGAGGCCC    2280
CGGAAATTGA CACTTATGGG CAGCAACGGA CATGAGTTTG TTTTCCTTCT AAAAGGCCAT    2340
```

-continued

```
GAAGATCTGC GCCAGGATGA GCGTGTGATG CAGCTCTTCG GCCTGGTTAA CACCCTTCTG      2400

GCCAATGACC CAACATCTCT TCGGAAAAAC CTCAGCATCC AGAGATACGC TGTCATCCCT      2460

TTATCGACCA ACTCGGGCCT CATTGGCTGG GTTCCCCACT GTGACACACT GCACGCCCTC      2520

ATCCGGGACT ACAGGGAGAA GAAGAAGATC CTTCTCAACA TCGAGCATCG CATCATGTTG      2580

CGGATGGCTC CGGACTATGA CCACTTGACT CTGATGCAGA AGGTGGAGGT GTTTGAGCAT      2640

GCCGTCAATA ATACAGCTGG GGACGACCTG GCCAAGCTGC TGTGGCTGAA AAGCCCCAGC      2700

TCCGAGGTGT GGTTTGACCG AAGAACCAAT TATACCCGTT CTTTAGCGGT CATGTCAATG      2760

GTTGGGTATA TTTTAGGCCT GGGAGATAGA CACCCATCCA ACCTGATGCT GGACCGTCTG      2820

AGTGGGAAGA TCCTGCACAT TGACTTTGGG GACTGCTTTG AGGTTGCTAT GACCCGAGAG      2880

AAGTTTCCAG AGAAGATTCC ATTTAGACTA ACAAGAATGT TGACCAATGC TATGGAGGTT      2940

ACAGGCCTGG ATGGCAACTA CAGAATCACA TGCCACACAG TGATGGAGGT GCTGCGAGAG      3000

CACAAGGACA GTGTCATGGC CGTGCTGGAA GCCTTTGTCT ATGACCCCTT GCTGAACTGG      3060

AGGCTGATGG ACACAAATAC CAAAGGCAAC AAGCGATCCC GAACGAGGAC GGATTCCTAC      3120

TCTGCTGGCC AGTCAGTCGA AATTTTGGAC GGTGTGGAAC TTGGAGAGCC AGCCCATAAG      3180

AAAACGGGGA CCACAGTGCC AGAATCTATT CATTCTTTCA TTGGGACGG TTTGGTGAAA       3240

CCAGAGGCCC TAAATAAGAA AGCTATCCAG ATTATTAACA GGGTTCGAGA TAAGCTCACT      3300

GGTCGGGACT TCTCTCATGA TGACACTTTG GATGTTCCAA CGCAAGTTGA GCTGCTCATC      3360

AAACAAGCGA CATCCCATGA AAACCTCTGC CAGTGCTATA TTGGCTGGTA CCCTTTCTGG      3420

TAA                                                                   3423
```

(2) INFORMATION FOR SEQ ID NO:3:

(i) SEQUENCE CHARACTERISTICS:
        (A) LENGTH: 2549 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Met Leu Gly Thr Gly Pro Ala Ala Ala Thr Thr Ala Ala Thr Thr Ser
1               5                  10                  15

Ser Asn Val Ser Val Leu Gln Gln Phe Ala Ser Gly Leu Lys Ser Arg
            20                  25                  30

Asn Glu Glu Thr Arg Ala Lys Ala Ala Lys Glu Leu Gln His Tyr Val
        35                  40                  45

Thr Met Glu Leu Arg Glu Met Ser Gln Glu Glu Ser Thr Arg Phe Tyr
    50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ala Thr Arg Ile Gly Arg Phe Ala Asn Tyr Leu Arg
            100                 105                 110

Asn Leu Leu Pro Ser Asn Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
```

-continued

```
               145                 150                 155                 160
Asn Glu Gly Arg Arg His Ala Ala Val Leu Val Leu Arg Glu Leu Ala
                    165                 170                 175
Ile Ser Val Pro Thr Phe Phe Gln Gln Val Gln Pro Phe Phe Asp
            180                 185                 190
Asn Ile Phe Val Ala Val Trp Asp Pro Lys Gln Ala Ile Arg Glu Gly
                195                 200                 205
Ala Val Ala Ala Leu Arg Ala Cys Leu Ile Leu Thr Thr Gln Arg Glu
            210                 215                 220
Pro Lys Glu Met Gln Lys Pro Gln Trp Tyr Arg His Thr Phe Glu Glu
225                 230                 235                 240
Ala Glu Lys Gly Phe Asp Glu Thr Leu Ala Lys Glu Lys Gly Met Asn
                245                 250                 255
Arg Asp Asp Arg Ile His Gly Ala Leu Leu Ile Leu Asn Glu Leu Val
                260                 265                 270
Arg Ile Ser Ser Met Glu Gly Glu Arg Leu Arg Glu Glu Met Glu Glu
            275                 280                 285
Ile Thr Gln Gln Gln Leu Val His Asp Lys Tyr Cys Lys Asp Leu Met
            290                 295                 300
Gly Phe Gly Thr Lys Pro Arg His Ile Thr Pro Phe Thr Ser Phe Gln
305                 310                 315                 320
Ala Val Gln Pro Gln Gln Ser Asn Ala Leu Val Gly Leu Leu Gly Tyr
                325                 330                 335
Ser Ser His Gln Gly Leu Met Gly Phe Gly Thr Ser Pro Ser Pro Ala
                340                 345                 350
Lys Ser Thr Leu Val Glu Ser Arg Cys Cys Arg Asp Leu Met Glu Glu
            355                 360                 365
Lys Phe Asp Gln Val Cys Gln Trp Val Leu Lys Cys Arg Asn Ser Lys
            370                 375                 380
Asn Ser Leu Ile Gln Met Thr Ile Leu Asn Leu Leu Pro Arg Leu Ala
385                 390                 395                 400
Ala Phe Arg Pro Ser Ala Phe Thr Asp Thr Gln Tyr Leu Gln Asp Thr
                405                 410                 415
Met Asn His Ala Leu Ser Cys Val Lys Lys Glu Lys Glu Arg Thr Ala
                420                 425                 430
Ala Phe Gln Ala Leu Gly Leu Leu Ser Val Ala Val Arg Ser Glu Phe
            435                 440                 445
Lys Val Tyr Leu Pro Arg Val Leu Asp Ile Ile Arg Ala Ala Leu Pro
            450                 455                 460
Pro Lys Asp Phe Ala His Lys Arg Gln Lys Ala Met Gln Val Asp Ala
465                 470                 475                 480
Thr Val Phe Thr Cys Ile Ser Met Leu Ala Arg Ala Met Gly Pro Gly
                485                 490                 495
Ile Gln Gln Asp Ile Lys Glu Leu Leu Glu Pro Met Leu Ala Val Gly
            500                 505                 510
Leu Ser Pro Ala Leu Thr Ala Val Leu Tyr Asp Leu Ser Arg Gln Ile
            515                 520                 525
Pro Gln Leu Lys Lys Asp Ile Gln Asp Gly Leu Leu Lys Met Leu Ser
            530                 535                 540
Leu Val Leu Met His Lys Pro Leu Arg His Pro Gly Met Pro Lys Gly
545                 550                 555                 560
Leu Ala His Gln Leu Ala Ser Pro Gly Leu Thr Thr Leu Pro Glu Ala
                565                 570                 575
```

-continued

```
Ser Asp Val Gly Ser Ile Thr Leu Ala Leu Arg Thr Leu Gly Ser Phe
            580                 585                 590

Glu Phe Glu Gly His Ser Leu Thr Gln Phe Val Arg His Cys Ala Asp
            595                 600                 605

His Phe Leu Asn Ser Glu His Lys Glu Ile Arg Met Glu Ala Ala Arg
            610                 615                 620

Thr Cys Ser Arg Leu Leu Thr Pro Ser Ile His Leu Ile Ser Gly His
625                 630                 635                 640

Ala His Val Val Ser Gln Thr Ala Val Gln Val Ala Asp Val Leu
                    645                 650                 655

Ser Lys Leu Leu Val Val Gly Ile Thr Asp Pro Asp Pro Asp Ile Arg
                    660                 665                 670

Tyr Cys Val Leu Ala Ser Leu Asp Glu Arg Phe Asp Ala His Leu Ala
                    675                 680                 685

Gln Ala Glu Asn Leu Gln Ala Leu Phe Val Ala Leu Asn Asp Gln Val
                    690                 695                 700

Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
                    725                 730                 735

Ile Leu Thr Glu Leu Glu His Ser Gly Ile Gly Arg Ile Lys Glu Gln
                    740                 745                 750

Ser Ala Arg Met Leu Gly His Leu Val Ser Asn Ala Pro Arg Leu Ile
                    755                 760                 765

Arg Pro Tyr Met Glu Pro Ile Leu Lys Ala Leu Ile Leu Lys Leu Lys
            770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
                    805                 810                 815

Val Asp Glu Leu Phe Ile Ile Ile Met Asp Met Leu Gln Asp Ser Ser
                    820                 825                 830

Leu Leu Ala Lys Arg Gln Val Ala Leu Trp Thr Leu Gly Gln Leu Val
                    835                 840                 845

Ala Ser Thr Gly Tyr Val Val Glu Pro Tyr Arg Lys Tyr Pro Thr Leu
850                 855                 860

Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
                    885                 890                 895

Tyr Lys His Lys Val Asn Ile Gly Met Ile Asp Gln Ser Arg Asp Ala
                    900                 905                 910

Ser Ala Val Ser Leu Ser Glu Ser Lys Ser Ser Gln Asp Ser Ser Asp
                    915                 920                 925

Tyr Ser Thr Ser Glu Met Leu Val Asn Met Gly Asn Leu Pro Leu Asp
            930                 935                 940

Glu Phe Tyr Pro Ala Val Ser Met Val Ala Leu Met Arg Ile Phe Arg
945                 950                 955                 960

Asp Gln Ser Leu Ser His His Thr Met Val Val Gln Ala Ile Thr
                    965                 970                 975

Phe Ile Phe Lys Ser Leu Gly Leu Lys Cys Val Gln Phe Leu Pro Gln
            980                 985                 990
```

```
Val Met Pro Thr Phe Leu Asn Val Ile Arg Val Cys Asp Gly Ala Ile
        995                 1000                1005

Arg Glu Phe Leu Phe Gln Gln Leu Gly Met Leu Val Ser Phe Val Lys
    1010                1015                1020

Ser His Ile Arg Pro Tyr Met Asp Glu Ile Val Thr Leu Met Arg Glu
1025                1030                1035                1040

Phe Trp Val Met Asn Thr Ser Ile Gln Ser Thr Ile Ile Leu Leu Ile
            1045                1050                1055

Glu Gln Ile Val Val Ala Leu Gly Gly Glu Phe Lys Leu Tyr Leu Pro
        1060                1065                1070

Gln Leu Ile Pro His Met Leu Arg Val Phe Met His Asp Asn Ser Pro
        1075                1080                1085

Gly Arg Ile Val Ser Ile Lys Leu Leu Ala Ala Ile Gln Leu Phe Gly
        1090                1095                1100

Ala Asn Leu Asp Asp Tyr Leu His Leu Leu Pro Pro Ile Val Lys
1105                1110                1115                1120

Leu Phe Asp Ala Pro Glu Ala Pro Leu Pro Ser Arg Lys Ala Ala Leu
            1125                1130                1135

Glu Thr Val Asp Arg Leu Thr Glu Ser Leu Asp Phe Thr Asp Tyr Ala
            1140                1145                1150

Ser Arg Ile Ile His Pro Ile Val Arg Thr Leu Asp Gln Ser Pro Glu
    1155                1160                1165

Leu Arg Ser Thr Ala Met Asp Thr Leu Ser Ser Leu Val Phe Gln Leu
    1170                1175                1180

Gly Lys Lys Tyr Gln Ile Phe Ile Pro Met Val Asn Lys Val Leu Val
1185                1190                1195                1200

Arg His Arg Ile Asn His Gln Arg Tyr Asp Val Leu Ile Cys Arg Ile
            1205                1210                1215

Val Lys Gly Tyr Thr Leu Ala Asp Glu Glu Asp Pro Leu Ile Tyr
        1220                1225                1230

Gln His Arg Met Leu Arg Ser Gly Gln Gly Asp Ala Leu Ala Ser Gly
            1235                1240                1245

Pro Val Glu Thr Gly Pro Met Lys Lys Leu His Val Ser Thr Ile Asn
    1250                1255                1260

Leu Gln Lys Ala Trp Gly Ala Ala Arg Arg Val Ser Lys Asp Asp Trp
1265                1270                1275                1280

Leu Glu Trp Leu Arg Arg Leu Ser Leu Glu Leu Leu Lys Asp Ser Ser
            1285                1290                1295

Ser Pro Ser Leu Arg Ser Cys Trp Ala Leu Ala Gln Ala Tyr Asn Pro
            1300                1305                1310

Met Ala Arg Asp Leu Phe Asn Ala Ala Phe Val Ser Cys Trp Ser Glu
            1315                1320                1325

Leu Asn Glu Asp Gln Gln Asp Glu Leu Ile Arg Ser Ile Glu Leu Ala
    1330                1335                1340

Leu Thr Ser Gln Asp Ile Ala Glu Val Thr Gln Thr Leu Leu Asn Leu
1345                1350                1355                1360

Ala Glu Phe Met Glu His Ser Asp Lys Gly Pro Leu Pro Leu Arg Asp
            1365                1370                1375

Asp Asn Gly Ile Val Leu Leu Gly Glu Arg Ala Ala Lys Cys Arg Ala
        1380                1385                1390

Tyr Ala Lys Ala Leu His Tyr Lys Glu Leu Glu Phe Gln Lys Gly Pro
        1395                1400                1405

Thr Pro Ala Ile Leu Glu Ser Leu Ile Ser Ile Asn Asn Lys Leu Gln
```

```
       1410               1415               1420
Gln Pro Glu Ala Ala Ala Gly Val Leu Glu Tyr Ala Met Lys His Phe
1425                1430                1435                1440

Gly Glu Leu Glu Ile Gln Ala Thr Trp Tyr Glu Lys Leu His Glu Trp
                1445                1450                1455

Glu Asp Ala Leu Val Ala Tyr Asp Lys Lys Met Asp Thr Asn Lys Asp
                1460                1465                1470

Asp Pro Glu Leu Met Leu Gly Arg Met Arg Cys Leu Glu Ala Leu Gly
                1475                1480                1485

Glu Trp Gly Gln Leu His Gln Gln Cys Cys Glu Lys Trp Thr Leu Val
                1490                1495                1500

Asn Asp Glu Thr Gln Ala Lys Met Ala Arg Met Ala Ala Ala Ala Ala
1505                1510                1515                1520

Trp Gly Leu Gly Gln Trp Asp Ser Met Glu Glu Tyr Thr Cys Met Ile
                1525                1530                1535

Pro Arg Asp Thr His Asp Gly Ala Phe Tyr Arg Ala Val Leu Ala Leu
                1540                1545                1550

His Gln Asp Leu Phe Ser Leu Ala Gln Gln Cys Ile Asp Lys Ala Arg
                1555                1560                1565

Asp Leu Leu Asp Ala Glu Leu Thr Ala Met Ala Gly Glu Ser Tyr Ser
                1570                1575                1580

Arg Ala Tyr Gly Ala Met Val Ser Cys His Met Leu Ser Glu Leu Glu
1585                1590                1595                1600

Glu Val Ile Gln Tyr Lys Leu Val Pro Glu Arg Arg Glu Ile Ile Arg
                1605                1610                1615

Gln Ile Trp Trp Glu Arg Leu Gln Gly Cys Gln Arg Ile Val Glu Asp
                1620                1625                1630

Trp Gln Lys Ile Leu Met Val Arg Ser Leu Val Val Ser Pro His Glu
                1635                1640                1645

Asp Met Arg Thr Trp Leu Lys Tyr Ala Ser Leu Cys Gly Lys Ser Gly
                1650                1655                1660

Arg Leu Ala Leu Ala His Lys Thr Leu Val Leu Leu Leu Gly Val Asp
1665                1670                1675                1680

Pro Ser Arg Gln Leu Asp His Pro Leu Pro Thr Val His Pro Gln Val
                1685                1690                1695

Thr Tyr Ala Tyr Met Lys Asn Met Trp Lys Ser Ala Arg Lys Ile Asp
                1700                1705                1710

Ala Phe Gln His Met Gln His Phe Val Gln Thr Met Gln Gln Gln Ala
                1715                1720                1725

Gln His Ala Ile Ala Thr Glu Asp Gln Gln His Lys Gln Glu Leu His
                1730                1735                1740

Lys Leu Met Ala Arg Cys Phe Leu Lys Leu Gly Glu Trp Gln Leu Asn
1745                1750                1755                1760

Leu Gln Gly Ile Asn Glu Ser Thr Ile Pro Lys Val Leu Gln Tyr Tyr
                1765                1770                1775

Ser Ala Ala Thr Glu His Asp Arg Ser Trp Tyr Lys Ala Trp His Ala
                1780                1785                1790

Trp Ala Val Met Asn Phe Glu Ala Val Leu His Tyr Lys His Gln Asn
                1795                1800                1805

Gln Ala Arg Asp Glu Lys Lys Lys Leu Arg His Ala Ser Gly Ala Asn
                1810                1815                1820

Ile Thr Asn Ala Thr Thr Ala Ala Thr Thr Ala Ala Thr Ala Thr Thr
1825                1830                1835                1840
```

-continued

```
Thr Ala Ser Thr Glu Gly Ser Asn Ser Glu Ser Glu Ala Glu Ser Thr
            1845                1850                1855
Glu Asn Ser Pro Thr Pro Ser Pro Leu Gln Lys Lys Val Thr Glu Asp
            1860                1865                1870
Leu Ser Lys Thr Leu Leu Met Tyr Thr Val Pro Ala Val Gln Gly Phe
            1875                1880                1885
Phe Arg Ser Ile Ser Leu Ser Arg Gly Asn Asn Leu Gln Asp Thr Leu
            1890                1895                1900
Arg Val Leu Thr Leu Trp Phe Asp Tyr Gly His Trp Pro Asp Val Asn
1905                1910                1915                1920
Glu Ala Leu Val Glu Gly Val Lys Ala Ile Gln Ile Asp Thr Trp Leu
            1925                1930                1935
Gln Val Ile Pro Gln Leu Ile Ala Arg Ile Asp Thr Pro Arg Pro Leu
            1940                1945                1950
Val Gly Arg Leu Ile His Gln Leu Leu Thr Asp Ile Gly Arg Tyr His
            1955                1960                1965
Pro Gln Ala Leu Ile Tyr Pro Leu Thr Val Ala Ser Lys Ser Thr Thr
            1970                1975                1980
Thr Ala Arg His Asn Ala Ala Asn Lys Ile Leu Lys Asn Met Cys Glu
1985                1990                1995                2000
His Ser Asn Thr Leu Val Gln Gln Ala Met Met Val Ser Glu Glu Leu
            2005                2010                2015
Ile Arg Val Ala Ile Leu Trp His Glu Met Trp His Glu Gly Leu Glu
            2020                2025                2030
Glu Ala Ser Arg Leu Tyr Phe Gly Glu Arg Asn Val Lys Gly Met Phe
            2035                2040                2045
Glu Val Leu Glu Pro Leu His Ala Met Met Glu Arg Gly Pro Gln Thr
            2050                2055                2060
Leu Lys Glu Thr Ser Phe Asn Gln Ala Tyr Gly Arg Asp Leu Met Glu
2065                2070                2075                2080
Ala Gln Glu Trp Cys Arg Lys Tyr Met Lys Ser Gly Asn Val Lys Asp
            2085                2090                2095
Leu Thr Gln Ala Trp Asp Leu Tyr Tyr His Val Phe Arg Arg Ile Ser
            2100                2105                2110
Lys Gln Leu Pro Gln Leu Thr Ser Leu Glu Leu Gln Tyr Val Ser Pro
            2115                2120                2125
Lys Leu Leu Met Cys Arg Asp Leu Glu Leu Ala Val Pro Gly Thr Tyr
            2130                2135                2140
Asp Pro Asn Gln Pro Ile Ile Arg Ile Gln Ser Ile Ala Pro Ser Leu
2145                2150                2155                2160
Gln Val Ile Thr Ser Lys Gln Arg Pro Arg Lys Leu Thr Leu Met Gly
            2165                2170                2175
Ser Asn Gly His Glu Phe Val Phe Leu Leu Lys Gly His Glu Asp Leu
            2180                2185                2190
Arg Gln Asp Glu Arg Val Met Gln Leu Phe Gly Leu Val Asn Thr Leu
            2195                2200                2205
Leu Ala Asn Asp Pro Thr Ser Leu Arg Lys Asn Leu Ser Ile Gln Arg
            2210                2215                2220
Tyr Ala Val Ile Pro Leu Ser Thr Asn Ser Gly Leu Ile Gly Trp Val
2225                2230                2235                2240
Pro His Cys Asp Thr Leu His Ala Leu Ile Arg Asp Tyr Arg Glu Lys
            2245                2250                2255
```

-continued

```
Lys Lys Ile Leu Leu Asn Ile Glu His Arg Ile Met Leu Arg Met Ala
            2260                2265                2270

Pro Asp Tyr Asp His Leu Thr Leu Met Gln Lys Val Glu Val Phe Glu
        2275                2280                2285

His Ala Val Asn Asn Thr Ala Gly Asp Leu Ala Lys Leu Leu Trp
    2290                2295                2300

Leu Lys Ser Pro Ser Ser Glu Val Trp Phe Asp Arg Arg Thr Asn Tyr
2305                2310                2315                2320

Thr Arg Ser Leu Ala Val Met Ser Met Val Gly Tyr Ile Leu Gly Leu
        2325                2330                2335

Gly Asp Arg His Pro Ser Asn Leu Met Leu Asp Arg Leu Ser Gly Lys
            2340                2345                2350

Ile Leu His Ile Asp Phe Gly Asp Cys Phe Glu Val Ala Met Thr Arg
        2355                2360                2365

Glu Lys Phe Pro Glu Lys Ile Pro Phe Arg Leu Thr Arg Met Leu Thr
        2370                2375                2380

Asn Ala Met Glu Val Thr Gly Leu Asp Gly Asn Tyr Arg Ile Thr Cys
2385                2390                2395                2400

His Thr Val Met Glu Val Leu Arg Glu His Lys Asp Ser Val Met Ala
            2405                2410                2415

Val Leu Glu Ala Phe Val Tyr Asp Pro Leu Leu Asn Trp Arg Leu Met
            2420                2425                2430

Asp Thr Asn Thr Lys Gly Asn Lys Arg Ser Arg Thr Arg Thr Asp Ser
        2435                2440                2445

Tyr Ser Ala Gly Gln Ser Val Glu Ile Leu Asp Gly Val Glu Leu Gly
    2450                2455                2460

Glu Pro Ala His Lys Lys Thr Gly Thr Thr Val Pro Glu Ser Ile His
2465                2470                2475                2480

Ser Phe Ile Gly Asp Gly Leu Val Lys Pro Glu Ala Leu Asn Lys Lys
            2485                2490                2495

Ala Ile Gln Ile Ile Asn Arg Val Arg Asp Lys Leu Thr Gly Arg Asp
        2500                2505                2510

Phe Ser His Asp Asp Thr Leu Asp Val Pro Thr Gln Val Glu Leu Leu
        2515                2520                2525

Ile Lys Gln Ala Thr Ser His Glu Asn Leu Cys Gln Cys Tyr Ile Gly
        2530                2535                2540

Trp Tyr Pro Phe Trp
2545
```

(2) INFORMATION FOR SEQ ID NO:4:

(i) SEQUENCE CHARACTERISTICS:
        (A) LENGTH: 1140 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45
```

-continued

```
Gly Leu Glu Phe Pro Asn Leu Pro Tyr Tyr Ile Asp Gly Asp Val Lys
 50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Asp His Pro Pro Lys Ser Asp Leu Val Pro Arg
210                 215                 220

Gly Gly Ser Pro Gly Ile Ser Gly Gly Gly Gly Ile Leu Asp
225                 230                 235                 240

Asp Ser Met Ser Phe Lys Tyr Ala Ser Leu Cys Gly Lys Ser Gly Arg
                245                 250                 255

Leu Ala Leu Ala His Lys Thr Leu Val Leu Leu Gly Val Asp Pro
            260                 265                 270

Ser Arg Gln Leu Asp His Pro Leu Pro Thr Val His Pro Gln Val Thr
            275                 280                 285

Tyr Ala Tyr Met Lys Asn Met Trp Lys Ser Ala Arg Lys Ile Asp Ala
290                 295                 300

Phe Gln His Met Gln His Phe Val Gln Thr Met Gln Gln Ala Gln
305                 310                 315                 320

His Ala Ile Ala Thr Glu Asp Gln Gln His Lys Gln Glu Leu His Lys
                325                 330                 335

Leu Met Ala Arg Cys Phe Leu Lys Leu Gly Glu Trp Gln Leu Asn Leu
            340                 345                 350

Gln Gly Ile Asn Glu Ser Thr Ile Pro Lys Val Leu Gln Tyr Tyr Ser
            355                 360                 365

Ala Ala Thr Glu His Asp Arg Ser Trp Tyr Lys Ala Trp His Ala Trp
370                 375                 380

Ala Val Met Asn Phe Glu Ala Val Leu His Tyr Lys His Gln Asn Gln
385                 390                 395                 400

Ala Arg Asp Glu Lys Lys Lys Leu Arg His Ala Ser Gly Ala Asn Ile
                405                 410                 415

Thr Asn Ala Thr Thr Ala Ala Thr Thr Ala Thr Ala Thr Thr Thr
            420                 425                 430

Ala Ser Thr Glu Gly Ser Asn Ser Glu Ser Glu Ala Ser Thr Glu
            435                 440                 445

Asn Ser Pro Thr Pro Ser Pro Leu Gln Lys Lys Val Thr Glu Asp Leu
450                 455                 460

Ser Lys Thr Leu Leu Met Tyr Thr Val Pro Ala Val Gln Gly Phe Phe
```

-continued

```
         465                 470                 475                 480
     Arg Ser Ile Ser Leu Ser Arg Gly Asn Asn Leu Gln Asp Thr Leu Arg
                         485                 490                 495

Val Leu Thr Leu Trp Phe Asp Tyr Gly His Trp Pro Asp Val Asn Glu
                 500                 505                 510

Ala Leu Val Glu Gly Val Lys Ala Ile Gln Ile Asp Thr Trp Leu Gln
                 515                 520                 525

Val Ile Pro Gln Leu Ile Ala Arg Ile Asp Thr Pro Arg Pro Leu Val
             530                 535                 540

Gly Arg Leu Ile His Gln Leu Leu Thr Asp Ile Gly Arg Tyr His Pro
     545                 550                 555                 560

Gln Ala Leu Ile Tyr Pro Leu Thr Val Ala Ser Lys Ser Thr Thr Thr
                         565                 570                 575

Ala Arg His Asn Ala Ala Asn Lys Ile Leu Lys Asn Met Cys Glu His
                 580                 585                 590

Ser Asn Thr Leu Val Gln Gln Ala Met Met Val Ser Glu Glu Leu Ile
                 595                 600                 605

Arg Val Ala Ile Leu Trp His Glu Met Trp His Glu Gly Leu Glu Glu
                 610                 615                 620

Ala Ser Arg Leu Tyr Phe Gly Glu Arg Asn Val Lys Gly Met Phe Glu
     625                 630                 635                 640

Val Leu Glu Pro Leu His Ala Met Met Glu Arg Gly Pro Gln Thr Leu
                         645                 650                 655

Lys Glu Thr Ser Phe Asn Gln Ala Tyr Gly Arg Asp Leu Met Glu Ala
                         660                 665                 670

Gln Glu Trp Cys Arg Lys Tyr Met Lys Ser Gly Asn Val Lys Asp Leu
                 675                 680                 685

Thr Gln Ala Trp Asp Leu Tyr Tyr His Val Phe Arg Arg Ile Ser Lys
             690                 695                 700

Gln Leu Pro Gln Leu Thr Ser Leu Glu Leu Gln Tyr Val Ser Pro Lys
     705                 710                 715                 720

Leu Leu Met Cys Arg Asp Leu Glu Leu Ala Val Pro Gly Thr Tyr Asp
                         725                 730                 735

Pro Asn Gln Pro Ile Ile Arg Ile Gln Ser Ile Ala Pro Ser Leu Gln
                         740                 745                 750

Val Ile Thr Ser Lys Gln Arg Pro Arg Lys Leu Thr Leu Met Gly Ser
                 755                 760                 765

Asn Gly His Glu Phe Val Phe Leu Leu Lys Gly His Glu Asp Leu Arg
     770                 775                 780

Gln Asp Glu Arg Val Met Gln Leu Phe Gly Leu Val Asn Thr Leu Leu
     785                 790                 795                 800

Ala Asn Asp Pro Thr Ser Leu Arg Lys Asn Leu Ser Ile Gln Arg Tyr
                 805                 810                 815

Ala Val Ile Pro Leu Ser Thr Asn Ser Gly Leu Ile Gly Trp Val Pro
                 820                 825                 830

His Cys Asp Thr Leu His Ala Leu Ile Arg Asp Tyr Arg Glu Lys Lys
                 835                 840                 845

Lys Ile Leu Leu Asn Ile Glu His Arg Ile Met Leu Arg Met Ala Pro
     850                 855                 860

Asp Tyr Asp His Leu Thr Leu Met Gln Lys Val Glu Val Phe Glu His
     865                 870                 875                 880

Ala Val Asn Asn Thr Ala Gly Asp Asp Leu Ala Lys Leu Leu Trp Leu
                         885                 890                 895
```

```
Lys Ser Pro Ser Ser Glu Val Trp Phe Asp Arg Arg Thr Asn Tyr Thr
            900                 905                 910

Arg Ser Leu Ala Val Met Ser Met Val Gly Tyr Ile Leu Gly Leu Gly
            915                 920                 925

Asp Arg His Pro Ser Asn Leu Met Leu Asp Arg Leu Ser Gly Lys Ile
            930                 935                 940

Leu His Ile Asp Phe Gly Asp Cys Phe Glu Val Ala Met Thr Arg Glu
945                 950                 955                 960

Lys Phe Pro Glu Lys Ile Pro Phe Arg Leu Thr Arg Met Leu Thr Asn
                965                 970                 975

Ala Met Glu Val Thr Gly Leu Asp Gly Asn Tyr Arg Ile Thr Cys His
            980                 985                 990

Thr Val Met Glu Val Leu Arg Glu His Lys Asp Ser Val Met Ala Val
            995                 1000                1005

Leu Glu Ala Phe Val Tyr Asp Pro Leu Leu Asn Trp Arg Leu Met Asp
    1010                1015                1020

Thr Asn Thr Lys Gly Asn Lys Arg Ser Arg Thr Arg Thr Asp Ser Tyr
1025                1030                1035                1040

Ser Ala Gly Gln Ser Val Glu Ile Leu Asp Gly Val Glu Leu Gly Glu
            1045                1050                1055

Pro Ala His Lys Lys Thr Gly Thr Thr Val Pro Glu Ser Ile His Ser
            1060                1065                1070

Phe Ile Gly Asp Gly Leu Val Lys Pro Glu Ala Leu Asn Lys Lys Ala
            1075                1080                1085

Ile Gln Ile Ile Asn Arg Val Arg Asp Lys Leu Thr Gly Arg Asp Phe
    1090                1095                1100

Ser His Asp Asp Thr Leu Asp Val Pro Thr Gln Val Glu Leu Leu Ile
1105                1110                1115                1120

Lys Gln Ala Thr Ser His Glu Asn Leu Cys Gln Cys Tyr Ile Gly Trp
            1125                1130                1135

Tyr Pro Phe Trp
            1140

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Ile Leu Leu Asn Ile Glu His Arg
1               5

(2) INFORMATION FOR SEQ ID NO:6:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Leu Ile Arg Pro Tyr Met Glu Pro Ile Leu Lys
```

(2) INFORMATION FOR SEQ ID NO:7:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Asp Xaa Met Glu Ala Gln Glu
1               5
```

(2) INFORMATION FOR SEQ ID NO:8:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Gln Leu Asp His Pro Leu Pro Thr Val His Pro Gln Val Thr Tyr Ala
1               5                   10                  15
Tyr Met Lys
```

(2) INFORMATION FOR SEQ ID NO:9:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
CGATCGGTCG ACTGCAGCAC TTTGGGGATT GTGCTCTC                          38
```

(2) INFORMATION FOR SEQ ID NO:10:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
GCGGCCGCAG CTTTCTTCAT GCATGACAAC AGCCCAGGC                         39
```

(2) INFORMATION FOR SEQ ID NO:11:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GCGGCCGCAA GCTTCAAGTA TGCAAGCCTG TGCGGCAAGA                                40

(2) INFORMATION FOR SEQ ID NO:12:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CGATCGGTCG ACACCTTCTG CATCAGAGTC AAGTGGTCA                                 39

(2) INFORMATION FOR SEQ ID NO:13:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GCGGCCGCAA GCTTCCTCAG CTCACATCCT TAGAGCTGCA                                40

(2) INFORMATION FOR SEQ ID NO:14:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CGATCGGTCG ACTTATTACC AGAAAGGGCA CCAGCCAATA TA                             42

(2) INFORMATION FOR SEQ ID NO:15:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CGATCGGTCG ACCAGATGAG CACATCATAG CGCTGATGA                                 39

(2) INFORMATION FOR SEQ ID NO:16:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

CGATCGGTCG ACAAATTCAA AGCTGCCAAG CGTTCGGAG                                 39

(2) INFORMATION FOR SEQ ID NO:17:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:17:

GCGGCCGCAA GCTTTGGCTC GAGCAATGGG GCCAGGCA                    38

(2) INFORMATION FOR SEQ ID NO:18:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GCGGCCGCAA GCTTAAGATG CTTGGAACCG CACCTGCCG                   39

(2) INFORMATION FOR SEQ ID NO:19:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CGATCGGTCG ACCAGATGAG CACATCATAG CGCTGATGA                   39

(2) INFORMATION FOR SEQ ID NO:20:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GCGGCCGCAA GCTTTGGCTC GAGCAATGGG GCCAGGCA                    38

(2) INFORMATION FOR SEQ ID NO:21:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GCGGCCGCAA GCTTAAGATG CTTGGAACCG CACCTGCCG                   39

(2) INFORMATION FOR SEQ ID NO:22:

(i) SEQUENCE CHARACTERISTICS:
        (A) LENGTH: 39 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:22:

CGATCGGTCG ACAAATTCAA AGCTGCCAAG CGTTCGGAG                                      39

(2) INFORMATION FOR SEQ ID NO:23:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Asp Tyr Lys Asp Asp Asp Asp Lys
1               5
```